United States Patent
Uil et al.

(10) Patent No.: US 11,872,281 B2
(45) Date of Patent: Jan. 16, 2024

(54) ADENOVIRUS AND USES THEREOF

(71) Applicant: JANSSEN VACCINES & PREVENTION B.V., Leiden (NL)

(72) Inventors: Taco Gilles Uil, Amsterdam (NL); Soumitra Roy, Townsend, DE (US); Selina Khan, Leiden (NL); Jerôme H. H. V. Custers, Alphen aan den Rijn (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 752 days.

(21) Appl. No.: 16/760,269

(22) PCT Filed: Oct. 30, 2018

(86) PCT No.: PCT/EP2018/079704
§ 371 (c)(1),
(2) Date: Apr. 29, 2020

(87) PCT Pub. No.: WO2019/086450
PCT Pub. Date: May 9, 2019

(65) Prior Publication Data
US 2020/0323977 A1    Oct. 15, 2020

(30) Foreign Application Priority Data

Oct. 31, 2017 (EP) ..................................... 17199347

(51) Int. Cl.
*C12N 15/00* (2006.01)
*A61K 39/235* (2006.01)
*C12N 15/86* (2006.01)

(52) U.S. Cl.
CPC ............ *A61K 39/235* (2013.01); *C12N 15/86* (2013.01); *C12N 2710/10321* (2013.01); *C12N 2710/10322* (2013.01); *C12N 2710/10334* (2013.01); *C12N 2710/10342* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 5,559,099 A | 9/1996 | Wickham et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,891,690 A | 4/1999 | Massie |

(Continued)

FOREIGN PATENT DOCUMENTS

| | | |
|---|---|---|
| EP | 2 350 268 | 8/2011 |
| EP | 2 536 829 | 12/2012 |

(Continued)

OTHER PUBLICATIONS

Altschul et al., "Basic Local Alignment Search Tool," (1990) J. Mol. Biol. 215: 403-410.

(Continued)

*Primary Examiner* — M Franco G Salvoza
(74) *Attorney, Agent, or Firm* — Ice Miller LLP

(57) ABSTRACT

Provided herein are adenoviral nucleic acid sequences and adenoviral vectors comprising said nucleic acid sequences. The provided adenoviral vectors can be used to induce a protective immune response in a subject.

25 Claims, 20 Drawing Sheets

Specification includes a Sequence Listing.

(56) References Cited

U.S. PATENT DOCUMENTS

| | | | |
|---|---|---|---|
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |

FOREIGN PATENT DOCUMENTS

| | | |
|---|---|---|
| WO | 98/39411 | 9/1998 |
| WO | 01/36615 | 5/2001 |
| WO | 2002/22080 | 3/2002 |
| WO | 2003/000283 | 1/2003 |
| WO | 2003/104467 | 12/2003 |
| WO | 2004/037189 | 5/2004 |
| WO | 2005/071093 | 8/2005 |
| WO | 2006/040330 | 4/2006 |
| WO | 2007/104792 | 9/2007 |
| WO | 2009/073104 | 6/2009 |
| WO | 2010/086189 | 8/2010 |
| WO | 2001/02607 | 1/2011 |
| WO | 2011/130627 | 10/2011 |
| WO | 2013/016591 | 1/2013 |
| WO | 2013/052859 | 4/2013 |
| WO | 2013/173702 | 11/2013 |

OTHER PUBLICATIONS

Altschul et al., "Gapped BLAST and PSI-BLAST: a new generation of protein database search programs," (1997) Nucleic Acids Res. 25: 3389-3402.
Barnes E, et al., "Novel Adenovirus-Based Vaccines Induce Broad and Sustained T Cell Responses to HCV in Man," 2012 Science translational medicine 4: 115ra1.
Fallaux et al., "New Helper Cells and Matched Early Region 1-Deleted Adenovirus Vectors Prevent Generation of Replication-Competent Adenovirus," 1998, Hum Gene Ther 9: 1909-17.
Gao et al., "A Cell Line for High-Yield Production of E1-Deleted Adenovirus Vectors without the Emergence of Replication-Competent Virus," 2000, Hum Gene Ther 11: 213-19.
Havenga et al., "Novel replication-incompetent adenoviral B-group vectors: high vector stability and yield in PER.C6 cells," J. Gen. Virol. 87(8):2135-43 (2006).
Henikoff & Henikoff, Proc. Natl. Acad. Sci. USA 89:10915 (1989).
Karlin & Altschul, "Amino acid substitution matrices from protein blocks," Proc. Nat'l. Acad. Sci. USA, 90: 5873-5787 (1993).
Kovesdi et al., "Adenoviral Producer Cells," 2010, Viruses 2: 1681-703.
Letvin et al., "Prospects for Vaccine Protection Against HIV-1 Infection and AIDS," Ann. Rev. Immunol. 20:73 (2002).
Maizel et al., "The Polypeptides of Adenovirus," Virology, 36(1):115-25 (1968).
Needleman & Wunsch, "A General Method Applicable to the Search for Similarities in the Amino Acid Sequence of Two Proteins," J. Mol. Biol. 48:443 (1970).
Pearson & Lipman, "Improved tools for biological sequence comparison," Proc. Nat'l. Acad. Sci. USA 85:2444 (1988).
Peruzzi D, et al., A novel Chimpanzee serotype-based adenoviral vector as delivery tool for cancer vaccines, 2009 Vaccine 27: 1293-300.
Quinn KM, et al., "Comparative Analysis of the Magnitude, Quality, Phenotype, and Protective Capacity of Simian Immunodeficiency Virus Gag-Specific CD8 T Cells following Human-, Simian-, and Chimpanzee-Derived Recombinant Adenoviral Vector Immunization," 2013, J Immunol 190: 2720-35.

Shiver et al., "Replication-incompetent adenoviral vacccine vector elicits effective anti-immunodeficiency-virus immunity," Nature 415:331 (2002).
Shiver and Emini, "Recent Advances in the Development of HIV-1 Vaccines Using Replication-Incompetent Adenovirus Vectors," Ann. Rev. Med. 55:355 (2004).
Smith & Waterman, "Comparison of Biosequences," Adv. Appl. Math. 2:482 (1981).
Sprangers et al., "Quantifying Adenovirus-Neutralizing Antibodies by Luciferase Transgene Detection: Addressing Preexisting Immunity to Vaccine and Gene Therapy Vectors," 2003, J.Clin. Microbiol. 41:5046-5052.
Susan J. Morris et al., "Simian adenoviruses as vaccine vectors," Future Virology, 11(9):649-659, 2016.
R.R. Bradley et al., "Adenovirus Serotype 5 Neutralizing Antibodies Target both Hexon and Fiber following Vaccination and Natural Infection," Journal of Virology, 86(1):625-629, 2011.
S.C. Jacobs, "Characterization and manipulation of the human adenovirus 4 genome," Journal of General Virology, 85(11):3361-3366, 2004.
Roberts Diane M. et al., "Hexon-chimaeric adenovirus serotype 5 vectors circumvent pre-existing anti-vector immunity," Nature, Macmillan Journals Ltd., London, 441(7090):239-243, 2006.
Julio Alonso-Padilla et al., "Development of Novel Adenoviral Vectors to Overcome Challenges Observed with HAdV-5-based Constructs," Molecular Therapy: The Journal of the American Society of Gene Therapy, 24(1):6-16, 2015.
Mohan Babu Appaiahgari et al., "Adenoviruses as gene/vaccine delivery vectors: promises and pitfalls," Expert Opinion on Biological Therapy, 15(3):337-351, 2014.
Abbink et al., "Comparative Seroprevalence and Immunogenicity of Six Rare Serotype Recombinant Adenovirus Vaccine Vectors from Subgroups B and D," Journal of Virology, 81(9):4654-4663, 2007.
Alba et al., "Vector Systems for Prenatal Gene Therapy: Principles of Adenovirus Design and Production," Methods in Molecular Biology, 891:55-84, 2012.
Bradley, et al., "Adenovirus Serotype 5-Specific Neutralizing Antibodies Target Multiple Hexon Hypervariable Regions," Journal of Virology, 86:1267-72, 2012.
Bruder et al., "Modification of Ad5 Hexon Hypervaribable Regions Circumvents Pre-Existing Ad5 Neutralizing Antibodies and Induces Protective Immune Responses," PLoS ONE, 7(4):e33920, 2012.
Gall et al., "Construction and Characterization of Hexon-Chimeric Adenoviruses: Specification of Adenovirus Serotype," Journal of Virology, 72(12):10260-10264, 1998.
Ma et al., "Synergistic suppression effect on tumor growth of hepatocellular carcinoma by combining oncolytic adenovirus carrying XAF1 with cisplatin," J Cancer Res Clin Oncol, 141:419-429, 2015.
Roy et al., "Circumvention of Immunity to the Adenovirus Major Coat Protein Hexon," Journal of Virology, 72(8):6875-6879, 1998.
Roy et al., "Use of chimeric adenoviral vectors to assess capsid neutralization determinants," Virology, 333:207-214, 2005.
Wu et al., "Construction and Characterization of Adenovirus Serotype 5 Packages by Serotype 3 Hexon," Journal of Virology, 76(24):12775-12782, 2002.
Youil et al., "Hexon Gene Switch Strategy for the Generation of Chimeric Recombinant Adenovirus," Human Gene Therapy, 13:311-320, 2002.
Yu et al., "Chimeric hexon HVRs protein reflects partial function of adenovirus," Biochemical and Biophysical Research Communication, 421:170-176, 2012.
Wevers et al., "Novel Adenoviruses in Wild Primates: a High Level of Genetic Diversity and Evidence of Zoonotic Transmissions," Journal of Virology, 85(20):10774-10784, 2011.
Ma et al., "Manipulating Adenovirus Hexon Hypervariable Loops Dictates Immune Neutralisation and Coagulation Factor X-dependent Cell Interaction In Vitro and In Vivo," PLoS Pathog, 11(2):e1004673, 2015.

```
BB21 fiber         MSKKRARVDD GFDPVYPYDA DNAPTVPFIN PPFVSSDGFQ EKPLGVLSLR  50
BB21 fiber variant ........................................................  50
BB24 fiber         ........................................................  50

BB21 fiber         LADPVTTKNG AVTLKLGEGV DLDDSGKLIS KNATKATAPL SISNNTISLN 100
BB21 fiber variant ........................................................ 100
BB24 fiber         ........................................................ 100

BB21 fiber         MDAPLYNNNG KLGIRIGAPL KVVDLLNTLA VAYGSGLGLK NNALTVQLVS 150
BB21 fiber variant ..........................▓............................. 150
BB24 fiber         ........................................................ 150

BB21 fiber         PLTFDNKGNV KINLGNGPLT VAANRLSVTC KRGLYVTTTG DALESNISWA 200
BB21 fiber variant ........................................................ 200
BB24 fiber         ........................................................ 200

BB21 fiber         KGIRFEGNAI AANIGKGLEF GTTSSESDVS NAYPIQVKLG TGLTFDSTGA 250
BB21 fiber variant ........................................................ 250
BB24 fiber         ........................................................ 250

BB21 fiber         IVAWNKEDDK LTLWTTADPS PNCKIYSEKD AKLTLCLTKC GSQILGTVTV 300
BB21 fiber variant ........................................................ 300
BB24 fiber         ........................................................ 300

BB21 fiber         LAVNNGSLNP ITNAVSTAIV YLKFDANGVL LSNSTLNKEY WNFRKGDVTP 350
BB21 fiber variant ..........▓............................................. 350
BB24 fiber         ........................................................ 350

BB21 fiber         AEAYTNAIGF MPNIKAYPKN TNVASKSHIV GQVYLNGDET KPLMLIITFN 400
BB21 fiber variant ........................................................ 400
BB24 fiber         ........................................................ 400

BB21 fiber         ETDDATCTYC ITFQWKWDNS KYTGETLATS SFPFSYIAQE 440
BB21 fiber variant .........▓................................. 440
BB24 fiber         ........................................... 440
```

FIG. 16

ADENOVIRUS AND USES THEREOF

CROSS-REFERENCE TO RELATED APPLICATIONS

This application is a Section 371 of International Application No. PCT/EP2018/079704, filed Oct. 30, 2018, which was published in the English language on May 9, 2019 under International Publication No. WO 2019/086450 A1, and claims priority under 35 U.S.C. § 119(b) to European Application No. 17199347.0, filed Oct. 31, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web and an ASCII formatted sequence listing with a file name "065768.11649_SL", creation date of Apr. 29, 2020, and having a size of 1,549 KB. The sequence listing submitted via EFS-Web is part of the specification and is herein incorporated by reference in its entirety.

FIELD OF THE INVENTION

This invention relates to biotechnology. More particularly, to the field and use of adenoviral vectors, such as replication defective adenoviral vectors to deliver antigens and elicit an immune response in hosts.

BACKGROUND OF THE INVENTION

Recombinant adenoviral vectors are widely applied for gene therapy applications and vaccines. AdV-5 vector-based vaccines have been shown to elicit potent and protective immune responses in a variety of animal models (see, e.g., WO2001/02607; WO2002/22080; Shiver et al., Nature 415: 331 (2002); Letvin et al., Ann. Rev. Immunol. 20:73 (2002); Shiver and Emini, Ann. Rev. Med. 55:355 (2004)). However, the utility of recombinant AdV-5 vector-based vaccines will likely be limited by the high seroprevalence of AdV-5-specific neutralizing antibodies (NAbs) in human populations. The existence of anti-AdV-5 immunity has been shown to substantially suppress the immunogenicity of AdV-5-based vaccines in studies in mice, rhesus monkeys, and humans.

One promising strategy to circumvent the existence of pre-existing immunity in individuals previously infected or treated with the most common human adenovirus, e.g., AdV-5, involves the development of recombinant vectors from adenovirus serotypes that do not encounter such pre-existing immunities. One such strategy is based on the use of non-human simian adenoviruses since these do not typically infect humans and exhibit low seroprevalence in human samples. Non-human simian adenoviruses are applicable for human use since it was shown that these viruses could infect human cells in vitro (WO2003/000283; WO2004/037189).

Thus, there is a need in the field for alternative adenoviral vectors that are producible in large quantities, that do not encounter pre-existing immunities in the host, but that are still immunogenic and capable of inducing a strong immune response against the antigens encoded by the heterologous nucleic acids inserted in the vector.

BRIEF SUMMARY OF THE INVENTION

Provided herein are isolated nucleic acid sequences. The isolated nucleic acid sequences encode a fiber polypeptide with at least 98% identity to amino acids 6-375 of SEQ ID NO:2. In certain embodiments, the fiber polypeptide comprises the amino acid sequence selected from a BB21 fiber polypeptide (SEQ ID NO:2), a BB21 fiber variant polypeptide (SEQ ID NO:3), or a BB24 fiber polypeptide (SEQ ID NO:4). In certain embodiments, the isolated nucleic acid sequence further comprises a hexon nucleic acid sequence encoding a hexon polypeptide comprising hexon hypervariable regions having the amino acid sequence selected from SEQ ID NO:5 or SEQ ID NO:6. In certain embodiments, the hexon polypeptide comprises the amino acid sequence selected from a BB21 hexon polypeptide (SEQ ID NO:7) or a BB24 hexon polypeptide (SEQ ID NO:8).

Also provided are isolated nucleic acid sequences encoding a hexon polypeptide comprising a hexon hypervariable regions-encompassing polypeptide having an amino acid sequence selected from SEQ ID NO:5 or SEQ ID NO:6. In certain embodiments, the hexon polypeptide comprises the amino acid sequence selected from a BB21 hexon polypeptide (SEQ ID NO:7) or a BB24 hexon polypeptide (SEQ ID NO:8).

Embodiments of the invention also include isolated fiber and hexon polypeptides encoded by the fiber and hexon nucleic acid sequences of the invention.

In certain embodiments, provided herein are isolated nucleic acids comprising a hexon nucleic acid sequence encoding at least one of the hexon polypeptides disclosed herein, and a nucleic acid sequence encoding at least one of the fiber polypeptides disclosed herein. In certain embodiments, provided herein are vectors comprising the isolated nucleic acids described herein. In one embodiment, the vector is a viral vector. In another embodiment, the vector is an expression vector. In one preferred embodiment, the vector is an adenoviral vector. More preferably, the vector further comprises a transgene.

Also provided are recombinant cells comprising the vectors described herein. Such cells can be used for recombinant protein production, recombinant protein expression, or the production of vectors or viral particles. Also provided are methods of producing a vector. The methods comprise (a) growing the recombinant cell disclosed herein under conditions for production of the vector; and (b) isolating the vector from the recombinant cell.

In certain embodiments, provided are immunogenic compositions comprising the vectors disclosed herein. Also provided are methods of inducing an immune response in a subject in need thereof, comprising administering to the subject the immunogenic compositions disclosed herein.

Further provided are adenoviral vectors comprising (a) at least one transgene insertion site; and (b) a nucleic acid sequence encoding a fiber polypeptide, wherein the fiber polypeptide comprises an amino acid sequence with at least 98% identity to amino acids 6-375 of SEQ ID NO:2. In certain embodiments, the fiber polypeptide comprises the amino acid sequence selected from a BB21 fiber polypeptide (SEQ ID NO:2), a BB21 fiber variant polypeptide (SEQ ID NO:3), or a BB24 fiber polypeptide (SEQ ID NO:4). In certain embodiments, adenoviral vector further comprises a hexon nucleic acid sequence encoding a hexon polypeptide comprising a hexon hypervariable regions-encompassing polypeptide having the amino acid sequence selected from SEQ ID NO:5 or SEQ ID NO:6. In certain embodiments, the hexon polypeptide comprises the amino acid sequence selected from a BB21 hexon polypeptide (SEQ ID NO:7) or a BB24 hexon polypeptide (SEQ ID NO:8).

Further provided are adenoviral vectors comprising (a) at least one transgene insertion site; and (b) a nucleic acid sequence encoding a hexon polypeptide, wherein the hexon polypeptide comprises a hexon hypervariable regions-encompassing polypeptide having the amino acid sequence selected from SEQ ID NO:5 or SEQ ID NO:6. In certain embodiments, the hexon polypeptide comprises the amino acid sequence selected from a BB21 hexon polypeptide (SEQ ID NO:7) or a BB24 hexon polypeptide (SEQ ID NO:8).

In certain embodiments, the adenoviral vectors provided herein are replication-defective adenovirus vectors (rAd). In one embodiment, the adenoviral vectors can comprise an E1 deletion. In certain embodiments, the adenoviral vectors provided herein can further comprise an E3 deletion. The adenoviral vectors can be simian adenoviral vectors comprising adenoviral nucleic acid sequences from one or more simian adenoviruses (SAdV), such as chimpanzee adenoviruses (e.g., ChAd3); gorilla adenoviruses; or rhesus adenoviruses (e.g., rhAd51, rhAd52 or rhAd53). The adenoviral vectors can be human adenoviral vectors comprising adenoviral sequences from one or more human adenoviruses (e.g., hAdV-4, hAdV-5, hAdV-26, hAdV-35). Preferably, the adenoviral vector is a chimeric adenoviral vector comprising one or more human adenoviral nucleic acid sequences. The human adenoviral nucleic acid sequences can, for example, be from human adenovirus-4 (hAdV-4), human adenovirus-5 (hAdV-5), human adenovirus-26 (hAdV-26), or human adenovirus-35 (hAdV-35). The adenoviral vectors can, for example, comprise a human adenovirus-5 (hAdV-5) E4 orf6 and orf 6/7.

In certain embodiments, the transgene insertion site is adjacent to an inverted terminal repeat (ITR). In certain embodiments, a transgene is inserted at one or more transgene insertion sites selected from the group consisting of a transgene insertion site at or adjacent to the E1 deletion, a transgene insertion site at or adjacent to the E3 deletion, and the transgene insertion site adjacent to the ITR, e.g., in between the E4 region and the right ITR (RITR).

In certain embodiments, the adenoviral vectors provided herein comprise a nucleic acid sequence selected from the group consisting of SEQ ID NO:28, SEQ ID NO:29, SEQ ID NO:30, SEQ ID NO:31, SEQ ID NO:53, and SEQ ID NO:57.

Also provided are immunogenic compositions or vaccines comprising the adenoviral vectors described herein and a pharmaceutically acceptable carrier. Further provided are methods for inducing an immune response in a subject in need thereof. The methods comprise administering to the subject the vaccines disclosed herein. Further provided are methods of producing a vaccine. The methods comprise combining an adenoviral vector disclosed herein with a pharmaceutically acceptable carrier.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows the experimental set-up, this setup was also used for the experiments shown in FIG. 2 and FIG. 3. FIG. 1B shows a graph of the cellular immune responses induced by Ad26.FLuc, BB21.FLuc and BB24.FLuc against the vector-encoded antigen (i.e. Fluc, firefly luciferase) as determined by Interferon gamma (IFN-γ) ELISPOT analysis. The y-axis shows the number of Spot Forming Units (SFU) per $10^6$ splenocytes and the dotted line indicates 95% percentile of the medium stimuli.

FIG. 4A shows the experimental set-up, this setup was also used for the experiments shown in FIG. 5 and FIG. 6. FIG. 4B shows results of a respiratory syncytial virus neutralization assay (VNA) performed at eight weeks after immunization with Ad26.RSVF-2A-GLuc and with BB21.RSVF-2A-GLuc at three different concentrations ($10^8$, $10^9$ and $10^{10}$ vp), or with Ad26.FLuc and BB21.FLuc at $10^{10}$ vp. The graph depicts VNA titers against respiratory syncytial virus strain A2 (RSV A2) calculated as endpoint titers ($\log_2$). FIG. 4C shows the cellular immune responses induced by Ad26.RSVF-2A-GLuc and BB21.RSVF-2A-GLuc against the vector-encoded antigen RSV F as determined by IFN-γ ELISPOT analysis. FIG. 4D shows a graph of RSV F-specific IgG binding antibody titers induced by Ad26.RSVF-2A-GLuc and BB21.RSVF-2A-GLuc in serum of immunized mice at 8 weeks post-immunization. The graph depicts IgG ELISA titers calculated as endpoint titers ($\log_{10}$).

FIG. 5A shows results of a respiratory syncytial virus neutralization assay (VNA) performed at eight weeks after immunization with Ad26.RSVF-2A-GLuc, BB24.RSVF-2A-GLuc and Ad48.RSVF-2A-GLuc at three different concentrations ($10^8$, $10^9$ and $10^{10}$vp), or with Ad26.FLuc, BB24.FLuc and Ad48.FLuc at $10^{10}$ vp. The graph depicts VNA titers against RSV A2 calculated as endpoint titers ($\log_2$). FIG. 5B shows the cellular immune response induced by Ad26.RSVF-2A-GLuc, BB24.RSVF-2A-GLuc and Ad48.RSVF-2A-GLuc against the vector-encoded antigen RSV F as determined by IFN-γ ELISPOT analysis. FIG. 5C shows a graph of RSV F-specific IgG binding antibody titers induced by Ad26.RSVF-2A-GLuc, BB24.RSVF-2A-GLuc and Ad48.RSVF-2A-GLuc in serum of immunized mice at 8 weeks post-immunization. The graph depicts IgG ELISA titers calculated as endpoint titers ($\log_{10}$).

FIG. 6A shows results of a respiratory syncytial virus neutralization assay (VNA) performed at eight weeks after immunization with Ad26.RSVF-2A-GLuc, Ad4Ptr01-BB24.RSVF-2A-GLuc and Ad4Ptr13-BB21.RSVF-2A-GLuc at three different concentrations ($10^8$, $10^9$ and $10^{10}$ vp), or with Ad26.FLuc, Ad4Ptr01-BB24.FLuc and Ad4Ptr13-BB21.FLuc at $10^{10}$ vp. The graph depicts VNA titers against RSV A2 calculated as endpoint titers ($\log_2$). FIG. 6B shows the cellular immune response induced by Ad26.RSVF-2A-GLuc, Ad4Ptr01-BB24.RSVF-2A-GLuc and Ad4Ptr13-BB21.RSVF-2A-GLuc against the vector-encoded antigen RSV F as determined by IFN-γ ELISPOT analysis. FIG. 6C shows a graph of RSV F-specific IgG binding antibody titers induced by Ad26.RSVF-2A-GLuc, Ad4Ptr01-BB24.RSVF-2A-GLuc and Ad4Ptr13-BB21.RSVF-2A-GLuc in serum of immunized mice at 8 weeks post-immunization. The graph depicts IgG ELISA titers calculated as endpoint titers ($\log_{10}$).

FIG. 16 shows an alignment of BB21 fiber (SEQ ID NO:2), BB21 fiber variant (SEQ ID NO:3), and BB24 fiber (SEQ ID NO:4).

DETAILED DESCRIPTION OF THE INVENTION

Figure 1A:
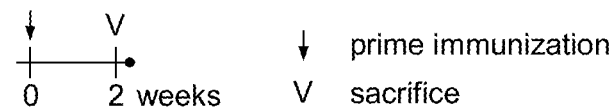
FIG. 1A-FIG. 1B show cellular immune responses induced by BB21.FLuc and BB24.FLuc.

This disclosure is based upon, at least in part, the isolation and identification of new chimpanzee adenovirus isolates, allocated into human adenovirus species E, as well as construction and evaluation of vaccine vectors comprising the nucleic acids encoding variable regions of the chimpanzee hexon and fiber polypeptides. This disclosure is additionally based upon, at least in part, the creation of chimeric adenoviral vectors comprising a human adenovirus backbone and at least one of a chimeric hexon or fiber polypeptide sequences or chimpanzee hexon or fiber polypeptide sequences. The adenoviral vectors are capable of eliciting an immune response and, furthermore, have low seroprevalence in humans. The adenoviral vectors can be formulated for vaccines and used to induce protective immunity against specific antigens of interest.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human, to whom will be or has been vaccinated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right", "left", "lower" and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., hexon and fiber polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, the term "protective immunity" or "protective immune response" means that the vaccinated subject is able to control an infection with the pathogenic agent against which the vaccination was done. The pathogenic agent can, for example, be an antigenic gene product or antigenic protein, or a fragment thereof. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

The term "adjuvant" is defined as one or more substances that cause stimulation of the immune system. In this context, an adjuvant is used to enhance an immune response to the adenovirus vectors of the invention.

As used herein, the term "antigenic gene product or fragment thereof" or "antigenic protein" can include a bacterial, viral, parasitic, or fungal protein, or a fragment thereof. Preferably, an antigenic protein or antigenic gene product is capable of raising in a host a protective immune response, e.g., inducing an immune response against a disease or infection (e.g., a bacterial, viral, parasitic, or fungal disease or infection), and/or producing an immunity in (i.e., vaccinating) a subject against a disease or infection, that protects the subject against the disease or infection.

Adenoviral Vectors

Exposure to certain adenoviruses has resulted in immune responses against certain adenoviral serotypes, which can affect efficacy of adenoviral vectors. Because infections with human adenoviruses are common in humans, the prevalence of neutralizing antibodies against human adenoviruses in human populations is high. The presence of such neutralizing antibodies in individuals may be expected to reduce the efficacy of a gene transfer vector based on a human adenoviral backbone. One way to circumvent the reduction of efficacy is to replace the epitopes on the adenoviral capsid proteins that are the targets of neutralizing antibodies. The target sequences on the capsid proteins can be replaced with protein sequences from other adenoviruses which are of low prevalence, and therefore against which neutralizing antibodies are rare in human populations.

A "capsid protein" refers to a protein on the capsid of an adenovirus (e.g., BB21, BB24, HAdV-4) or a functional fragment or derivative thereof that is involved in determining the serotype and/or tropism of a particular adenovirus. Capsid proteins typically include the fiber, penton and/or hexon proteins. In certain embodiments, the capsid protein is an entire or full length capsid protein of the adenovirus. In other embodiments, the capsid protein is a fragment or a derivative of a full length capsid protein of the adenovirus. In certain embodiments, the hexon, penton and fiber encoded by an adenoviral vector of the invention are of the same or different adenoviral background (i.e., a BB21 hexon and a BB21 fiber, a BB24 hexon and a BB24 fiber, a PrtoAdV-1 hexon and a BB21 fiber variant, a PtroAdV-13 hexon and a BB24 fiber, etc).

A "hexon polypeptide" refers to adenovirus hexon coat proteins, functional fragments, and derivatives thereof.

A "fiber polypeptide" refers to adenovirus fiber proteins, functional fragments, and derivatives thereof.

One target of neutralizing antibodies against adenoviruses is the major coat protein, the hexon protein. Replacing the hexon protein or the variable sequences within the hexon protein, which define serotype and bind to neutralizing antibodies, with the hexon protein or variable sequences within the hexon protein from adenoviruses that are rare in the human population, such as those chimpanzee adenovirus sequences described herein, can allow for the construction of adenovirus vectors that would be less susceptible to neutralization by antibodies commonly found in humans.

A second target of neutralizing antibodies against adenoviruses is the fiber protein. Replacing the fiber protein or variable sequences within the fiber protein with the fiber protein or variable sequences within the fiber protein from adenoviruses that are rare in the human population, such as those chimpanzee adenovirus sequences described herein, can also allow for the construction of adenovirus vectors that would be less susceptible to neutralization by antibodies commonly found in humans. A combination of the fiber replacement with hexon replacements described above can confer additional resistance to neutralization by antibodies commonly present in human populations.

This disclosure provides isolated and chimeric nucleic acid sequences encoding hexon polypeptides and/or fiber polypeptides derived from isolated human and simian adenovirus serotypes and adenoviral vectors comprising at least one of the isolated and/or chimeric nucleic acid sequences.

An "adenoviral vector" refers to a recombinant vector derived from or containing at least a portion of an adenoviral genome.

In preferred embodiments, the isolated nucleic acid sequences encode a fiber polypeptide with at least 98% identity to amino acids 6-375 of SEQ ID NO:2. In certain embodiments, the isolated nucleic acid sequences encode a fiber polypeptide with at least 99% identity to amino acids 6-375 of SEQ ID NO:2. In certain embodiments, the isolated nucleic acid sequences encode a fiber polypeptide with at least 98%, 99% identity to SEQ ID NO:2. The fiber polypeptide can, for example, comprise an amino acid sequence selected from a BB21 fiber polypeptide (SEQ ID NO:2), a BB21 fiber variant polypeptide (SEQ ID NO:3), or a BB24 fiber polypeptide (SEQ ID NO:4). In certain preferred embodiments, the isolated nucleic acid sequence further comprises a nucleic acid sequence encoding a hexon polypeptide comprising a hexon polypeptide hypervariable regions-encompassing polypeptide comprising an amino acid sequence selected from SEQ ID NO:5 or SEQ ID NO:6. The hexon polypeptide can, for example, comprise an amino acid sequence selected from a BB21 hexon polypeptide (SEQ ID NO:7) or a BB24 hexon polypeptide (SEQ ID NO:8).

In preferred embodiments, the isolated nucleic acid sequences encode a hexon polypeptide comprising a polypeptide sequence comprising a hexon polypeptide hypervariable regions-encompassing polypeptide, wherein the hexon hypervariable regions-encompassing polypeptide comprises an amino acid sequence selected from SEQ ID NO:5 or SEQ ID NO:6. In certain embodiments, the hexon polypeptide comprises an amino acid sequence selected from a BB21 hexon polypeptide (SEQ ID NO:7) or a BB24 hexon polypeptide (SEQ ID NO:8).

In preferred embodiments, provided is an isolated nucleic acid comprising a hexon nucleic acid sequence encoding at least one of the hexon polypeptides disclosed herein and a nucleic acid sequence encoding at least one of the fiber polypeptides disclosed herein.

In preferred embodiments, provided are vectors, preferably adenoviral vectors, comprising at least one of an isolated nucleic acid sequence encoding a hexon polypeptide and/or an isolated nucleic acid sequence encoding a fiber polypeptide according to embodiments of the invention. The adenoviral vectors can, for example, comprise at least one transgene insertion site; and a nucleic acid sequence encoding a hexon polypeptide and/or a fiber polypeptide, wherein the hexon polypeptide comprises a polypeptide comprising a hexon polypeptide hypervariable regions-encompassing polypeptide disclosed herein and the fiber polypeptide comprises a fiber polypeptide described herein.

Typically, an adenoviral vector of the invention comprises the entire recombinant adenoviral genome on, e.g., a plasmid, cosmid, or baculovirus vector. The nucleic acid molecules of the invention can be in the form of RNA or in the form of DNA obtained by cloning or produced synthetically. The DNA can be double-stranded or single-stranded.

One of ordinary skill will recognize that elements derived from multiple serotypes can be combined in a single adenoviral vector, for example human or simian adenovirus. Thus, a chimeric adenovirus vector that combines desirable properties from different serotypes can be produced. Thus, in some embodiments, a chimeric adenovirus vector of the invention could combine the absence of pre-existing immunity of a simian hexon and/or fiber polypeptide sequences with the high level antigen delivery and presentation capacity of an existing adenoviral vectors, such as rAd4, rAd5, rAd26 or rAd35.

Advantages of adenoviral vectors for use as vaccines include ease of manipulation, good manufacturability at large scale, and an excellent safety record based on many years of experience in research, development, manufacturing and clinical trials with numerous adenoviral vectors that have been reported. Adenoviral vectors that are used as vaccines generally provide a good immune response to the transgene-encoded protein, including a cellular immune response. An adenoviral vector according to the invention can be based on any type of adenovirus, and in certain embodiments is a human adenovirus, which can be of any group or serotype. In preferred embodiments, the recombinant adenovirus is based upon a human adenovirus from group A, B, C, D, E, F or G. In other preferred embodiments, the recombinant adenovirus is based upon a human adenovirus serotype 5, 11, 26, 34, 35, 48, 49, or 50. In other embodiments, it is a simian adenovirus, such as chimpanzee or gorilla adenovirus, which can be of any serotype. In certain embodiments, the recombinant adenovirus is based upon chimpanzee adenovirus type 1, 3, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50, 67, or SA7P.

In a more preferred embodiment, the chimpanzee adenovirus vector of the second composition is ChAdV3. Recombinant chimpanzee adenovirus serotype 3 (ChAd3 or cAd3) is a subgroup C adenovirus with properties similar to those of human adenovirus serotype 5 (Ad5). ChAd3 has been shown to be safe and immunogenic in human studies evaluating candidate vaccines for hepatitis C virus (HCV) (Barnes E, et al. 2012 Science translational medicine 4: 115ra1). It was reported that ChAd3-based vaccines were capable of inducing an immune response comparable to a human Ad5 vectored vaccine. See, e.g., Peruzzi D, et al. 2009 Vaccine 27: 1293-300 and Quinn K M, et al. 2013 J Immunol 190: 2720-35; WO 2005/071093; and WO2011/0130627.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., *Scientific American Books* (1992), and Ausubel et al., *Current Protocols in Molecular Biology*, Wiley Interscience Publishers, NY (1995), and other references mentioned herein.

In certain embodiments, the adenoviral vector comprises an E1 deletion and/or an E3 deletion. An E1 or E3 deletion can, for example, include a complete deletion of the gene or a partial deletion, which renders the E1 or E3 gene product functionally defective. Thus, in certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented. One or more of the E1, E2, E3 and E4 regions can also be inactivated by other means, such as by inserting a transgene of interest (usually linked to a promoter) into the regions to be inactivated.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al., 2000, *Hum Gene Ther* 11: 213-19), 293, and the like. In certain embodiments, the producer cells are for instance HEK293 cells, or PER.C6 cells, or 911 cells, or IT293SF cells, and the like. Production of adenoviral vectors in producer cells is reviewed in (Kovesdi et al., 2010, *Viruses* 2: 1681-703).

In certain embodiments, the adenoviral vector is a chimeric adenoviral vector comprising one or more human adenoviral nucleic acid sequences. The human adenoviral nucleic acids can, for example, be selected from human adenovirus-4 (Ad-4), human adenovirus-5 (Ad-5), human adenovirus-26 (Ad-26), or human adenovirus-35 (Ad-35). In certain embodiments, an E1-deficient adenoviral vector comprises the E4-orf6 coding sequence of an adenovirus of human Ad5. This allows propagation of such adenoviruses in well-known complementing cell lines that express the E1 genes of Ad5, such as for example 293 cells or PER.C6 cells (see, e.g. Fallaux et al., 1998, *Hum Gene Ther* 9: 1909-17, Havenga et al., 2006, *J Gen Virol* 87: 2135-43; WO 03/104467, incorporated in their entirety by reference herein).

In certain embodiments, the adenoviral vector comprises a transgene. A "transgene" refers to a heterologous nucleic acid, which is a nucleic acid that is not naturally present in the vector, and according to the present invention the transgene can encode an antigenic gene product or antigenic protein that elicits an immune response in the subject. The transgene can, for example, be introduced into the vector by standard molecular biology techniques. The transgene can, for example, be cloned into a deleted E1 or E3 region of an adenoviral vector, or in the region between the E4 region and the rITR. A transgene is generally operably linked to expression control sequences. In preferred embodiments, the transgene is inserted at a transgene insertion site.

If required, the nucleic acid sequence encoding a hexon or fiber polypeptide according to embodiments of the invention, and/or the transgene can be codon-optimized to ensure proper expression in the treated host (e.g., human). Codon-optimization is a technology widely applied in the art.

The transgene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

In preferred embodiments, the adenoviral vector comprises a nucleic acid sequence selected from the group consisting of SEQ ID NO:28, SEQ ID NO:29, SEQ ID NO:30, SEQ ID NO:31, SEQ ID NO:53, and SEQ ID NO:57.

Immunogenic Compositions

Immunogenic compositions are compositions comprising an immunologically effective amount of purified or partially purified human or simian (e.g., chimpanzee) adenovirus vectors for use in the invention. Said compositions can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

The immunogenic compositions according to embodiments of the present invention can be made using methods known to those of skill in the art in view of the present disclosure. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The immunogenic compositions useful in the invention can comprise adjuvants. Adjuvants suitable for co-administration in accordance with the invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, AS01, AS03, AS04, AS15, GcMAF, B-alethine, MPC-026, Adjuvax, CpG ODN, Betafectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-10, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

Method for Inducing Protective Immunity

Another general aspect of the invention relates to a method of inducing an immune response in a subject in need thereof. The methods can, for example, comprise administering to the subject a vaccine comprising an adenoviral vector described herein and a pharmaceutically acceptable carrier. Also provided herein are methods of producing a vaccine. The methods comprise combining an adenoviral vector described herein with a pharmaceutically acceptable carrier.

Any of the immunogenic compositions according to embodiments of the invention, including but not limited to those described herein, can be used in methods of the invention as a vaccine.

Administration of the immunogenic compositions/vaccines comprising the vectors is typically intramuscular or subcutaneous. However other modes of administration such as intravenous, cutaneous, intradermal, genital, or nasal can be envisaged as well. Intramuscular administration of the immunogenic compositions can be achieved by using a needle to inject a suspension of the adenovirus vector. An alternative is the use of a needleless injection device to administer the composition (using, e.g., Biojector™) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration will have a prophylactic aim to generate an immune response against an antigen of interest (e.g., a bacterial, viral, parasitic, and/or fungal pathogen) before infection or development of symptoms. Diseases and disorders that can be treated or prevented in accordance with the invention include those in which an immune response can play a protective or therapeutic role. In other embodiments, the adenovirus vectors can be administered for post-exposure prophylactics.

The immunogenic compositions containing the human or simian (e.g., chimpanzee) adenovirus vectors are administered to a subject, giving rise to an immune response to the antigen of interest in the subject. An amount of a composition sufficient to induce a detectable immune response is defined to be an "immunologically effective dose" or an "effective amount" of the composition. The immunogenic compositions of the invention can induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the adenovirus vectors.

In one exemplary regimen, the adenoviral vector is administered (e.g., intramuscularly) in a volume ranging between about 100 µl to about 10 ml containing concentrations of about $10^4$ to $10^{12}$ virus particles/ml. Preferably, the adenoviral vector is administered in a volume ranging between 0.1 and 2.0 ml. For example, the adenoviral vector can be administered with 100 µl, 500 µl, 1 ml, 2 ml. More preferably the adenoviral vector is administered in a volume of 0.5 ml. Optionally, the adenoviral vector can be administered in a concentration of about $10^7$ vp/ml, $10^8$ vp/ml, $10^9$ vp/ml, $10^{10}$ vp/ml, $5\times10^{10}$ vp/ml, $10^{11}$ vp/ml, or $10^{12}$ vp/ml. Typically, the adenoviral vector is administered in an amount of about $10^9$ to about $10^{12}$ viral particles (vp) to a human subject during one administration, more typically in an amount of about $10^{10}$ to about $10^{12}$ vp.

The initial vaccination can be followed by a boost or a kick from a vaccine/composition comprising the same adenoviral vector encoding an antigen of interest or a vaccine/composition comprising a different adenoviral vector encoding the same antigen of interest.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

The compositions of the invention can be administered alone or in combination with other treatments, either simultaneously or sequentially dependent upon the condition to be treated.

EMBODIMENTS

The invention provides also the following non-limiting embodiments.

Embodiment 1 is an isolated nucleic acid sequence encoding a fiber polypeptide with at least 98% identity to amino acids 6-375 of SEQ ID NO:2.

Embodiment 2 is the isolated nucleic acid sequence of embodiment 1, wherein the fiber polypeptide comprises an amino acid sequence selected from a BB21 fiber polypeptide (SEQ ID NO:2), a BB21 fiber variant polypeptide (SEQ ID NO:3), or a BB24 fiber polypeptide (SEQ ID NO:4).

Embodiment 3 is an isolated nucleic acid of embodiment 1 or 2, wherein the isolated nucleic acid further comprises a nucleic acid sequence encoding a hexon polypeptide comprising a hexon hypervariable regions-encompassing polypeptide comprising an amino acid sequence selected from SEQ ID NO:5 or SEQ ID NO:6.

Embodiment 4 is the isolated nucleic acid of embodiment 3, wherein the hexon polypeptide comprises an amino acid sequence selected from a BB21 hexon polypeptide (SEQ ID NO:7) or a BB24 hexon polypeptide (SEQ ID NO:8).

Embodiment 5 is an isolated nucleic acid of embodiment 1 or 2, wherein the isolated nucleic acid further comprises a nucleic acid sequence encoding a hexon polypeptide comprising an amino acid sequence selected from a Ptr01 hexon polypeptide (SEQ ID NO:10) or a Ptr13 hexon polypeptide (SEQ ID NO:12).

Embodiment 6 is an isolated nucleic acid sequence encoding a hexon polypeptide comprising a hexon hypervariable regions-encompassing polypeptide comprising an amino acid sequence selected from SEQ ID NO:5 or SEQ ID NO:6.

Embodiment 7 is the isolated nucleic acid sequence of embodiment 6, wherein the hexon polypeptide comprises an amino acid sequence selected from a BB21 hexon polypeptide (SEQ ID NO:7) or a BB24 hexon polypeptide (SEQ ID NO:8).

Embodiment 8 is a vector comprising the nucleic acid of any one of embodiments 1-7.

Embodiment 9 is the vector of embodiment 8, being an adenoviral vector, and further comprising a transgene.

Embodiment 10 is a recombinant cell comprising the vector of embodiment 8 or 9.

Embodiment 11 is a method of producing a vector, comprising (a) growing the recombinant cell of embodiment 10 under conditions for production of the vector;

and (b) isolating the vector from the recombinant cell.

Embodiment 12 is an immunogenic composition comprising the vector of embodiment 8 or 9.

Embodiment 13 is a method of inducing an immune response in a subject in need thereof, comprising administering to the subject the immunogenic composition of embodiment 12.

Embodiment 14 is an adenoviral vector comprising (a) at least one transgene; and (b) a nucleic acid sequence encoding a fiber polypeptide, wherein the fiber polypeptide comprises an amino acid sequence with at least 98% identity to amino acids 6-375 of SEQ ID NO:2.

Embodiment 15 is the adenoviral vector of embodiment 14, wherein the fiber polypeptide comprises an amino acid sequence with at least 99% identity to amino acids 6-375 of SEQ ID NO:2.

Embodiment 16 is the adenoviral vector of embodiment 14 or 15, wherein the fiber polypeptide comprises an amino acid sequence with at least 98% identity to SEQ ID NO:2.

Embodiment 17 is the adenoviral vector of any one of embodiments 14-16, wherein the fiber polypeptide comprises an amino acid sequence with at least 99% identity to SEQ ID NO:2.

Embodiment 18 is the adenoviral vector of any one of embodiments 14-17, wherein the fiber polypeptide comprises an amino acid sequence selected from a BB21 fiber polypeptide (SEQ ID NO:2), a BB21 fiber variant polypeptide (SEQ ID NO:3), or a BB24 fiber polypeptide (SEQ ID NO:4).

Embodiment 19 is the adenoviral vector of any one of embodiments 14-18, further comprising a nucleic acid sequence encoding a hexon polypeptide comprising a hexon hypervariable regions-encompassing polypeptide comprising an amino acid sequence selected from SEQ ID NO:5 or SEQ ID NO:6.

Embodiment 20 is the adenoviral vector of embodiment 19, wherein the hexon polypeptide comprises an amino acid sequence selected from a BB21 hexon polypeptide (SEQ ID NO:7) or a BB24 hexon polypeptide (SEQ ID NO:8).

Embodiment 21 is an adenoviral vector comprising (a) at least one transgene insertion site; and (b) a nucleic acid sequence encoding a hexon polypeptide, wherein the hexon polypeptide comprises a hexon hypervariable regions-encompassing polypeptide comprising an amino acid sequence selected from SEQ ID NO:5 or SEQ ID NO:6.

Embodiment 22 is the adenoviral vector of embodiment 21, wherein the hexon polypeptide comprises an amino acid sequence selected from a BB21 hexon polypeptide (SEQ ID NO:7) or a BB24 hexon polypeptide (SEQ ID NO:8).

Embodiment 23 is the adenoviral vector of any one of embodiments 14-22, wherein the adenoviral vector further comprises an E1 deletion or an inactivated E1.

Embodiment 24 is the adenoviral vector of any one of embodiments 14-23, wherein the adenoviral vector further comprises an E3 deletion or an inactivated E3.

Embodiment 25 is the adenoviral vector of any one of embodiments 14-24, wherein the adenoviral vector is a chimeric adenoviral vector comprising one or more human adenoviral nucleic acid sequences.

Embodiment 26 is the adenoviral vector of embodiment 25, wherein the human adenoviral nucleic acid sequences are from human adenovirus-4 (hAdV-4), human adenovirus-5 (hAdV-5), human adenovirus-26 (hAdV-26), or human adenovirus-35 (hAdV-35).

Embodiment 27 is the adenoviral vector of embodiment 26, wherein the adenoviral vector comprises a human adenovirus-5 (hAdV-5) E4 orf6.

Embodiment 28 is the adenoviral vector of any one or embodiments 14-27, wherein the transgene insertion site is adjacent to an inverted terminal repeat (ITR).

Embodiment 29 is the adenoviral vector of embodiment 28, wherein a transgene is inserted at one or more transgene insertion sites selected from the group consisting of a transgene insertion site at the E1 deletion, a transgene insertion site at the E3 deletion, and the transgene insertion site adjacent to the ITR.

Embodiment 30 is the adenoviral vector of any one of embodiments 14-29, wherein the adenoviral vector comprises a nucleic acid sequence selected from the group consisting of SEQ ID NO:28, SEQ ID NO:29, SEQ ID NO:30, and SEQ ID NO:31.

Embodiment 31 is the adenoviral vector of any one of embodiments 14-18 and 23-29, wherein the adenoviral vector comprises a nucleic acid sequence selected from SEQ ID NO:53 or SEQ ID NO:57.

Embodiment 32 is an adenoviral vector comprising (a) at least one transgene; (b) a nucleic acid sequence encoding a hexon polypeptide comprising an amino acid sequence selected from the group consisting of BB21 hexon polypeptide (SEQ ID NO:7), a BB24 hexon polypeptide (SEQ ID NO:8), a Ptr01 hexon polypeptide (SEQ ID NO:10), a Ptr13 hexon polypeptide (SEQ ID NO:12), and (c) a nucleic acid sequence encoding a fiber polypeptide comprising an amino acid sequence selected from a BB21 fiber polypeptide (SEQ ID NO:2), a BB21 fiber variant polypeptide (SEQ ID NO:3), or a BB24 fiber polypeptide (SEQ ID NO:4).

Embodiment 33 is the adenoviral vector of embodiment 32, wherein the hexon polypeptide comprises the amino acid sequence of a Ptr01 hexon polypeptide (SEQ ID NO:10) or a Ptr13 hexon polypeptide (SEQ ID NO:12), and the fiber polypeptide comprises the amino acid sequence of a BB21 fiber polypeptide (SEQ ID NO:2), a BB21 fiber variant polypeptide (SEQ ID NO:3), or a BB24 fiber polypeptide (SEQ ID NO:4).

Embodiment 34 is the adenoviral vector of embodiment 33, wherein the hexon polypeptide comprises the amino acid sequence of the Ptr01 hexon polypeptide (SEQ ID NO:10) and the fiber polypeptide comprises the amino acid sequence of the BB24 fiber polypeptide (SEQ ID NO:4).

Embodiment 35 is the adenoviral vector of embodiment 33, wherein the hexon polypeptide comprises the amino acid sequence of the Ptr13 hexon polypeptide (SEQ ID NO:12) and the fiber polypeptide comprises the amino acid sequence of the BB21 fiber variant polypeptide (SEQ ID NO:3).

Embodiment 36 is the adenoviral vector of embodiment 32, wherein the hexon polypeptide comprises the amino acid sequence of a BB21 hexon polypeptide (SEQ ID NO:7), and the fiber polypeptide comprises the amino acid sequence of a BB21 fiber polypeptide (SEQ ID NO:2).

Embodiment 37 is the adenoviral vector of embodiment 32, wherein the hexon polypeptide comprises the amino acid sequence of a BB24 hexon polypeptide (SEQ ID NO:8), and the fiber polypeptide comprises the amino acid sequence of a BB24 fiber polypeptide (SEQ ID NO:4).

Embodiment 38 is the adenoviral vector of any of embodiments 32-37, wherein the adenoviral vector further comprises one or more nucleic acid sequences from human adenovirus-4 (HAdV-4), human adenovirus-5 (HAdV-5), human adenovirus-26 (HAdV-26), or human adenovirus-35 (HAdV-35).

Embodiment 39 is the adenoviral vector of embodiment 38, wherein the adenoviral vector comprises one or more nucleic acid sequences from human adenovirus-4 (HAdV-4) and a nucleic acid sequence of a human adenovirus-5 (HAdV-5) E4 orf6.

Embodiment 40 is the adenoviral vector of embodiment 39, comprising the nucleic acid sequence selected from the group consisting of SEQ ID NO:53 and SEQ ID NO:57.

Embodiment 41 is a vaccine comprising an adenoviral vector according to any of embodiments 14-40 and a pharmaceutically acceptable carrier.

Embodiment 42 is a method for inducing an immune response in a subject in need thereof, the method comprising administering to the subject the vaccine of embodiment 41.

Embodiment 43 is a method of producing a vaccine, comprising combining an adenoviral vector according to any of embodiment 14-40 with a pharmaceutically acceptable carrier.

Embodiment 44 is an isolated hexon polypeptide comprising a hexon hypervariable regions-encompassing polypeptide comprising an amino acid sequence selected from SEQ ID NO:5 or SEQ ID NO:6.

Embodiment 45 is the isolated hexon polypeptide of embodiment 44, wherein the hexon polypeptide comprises an amino acid sequence selected from a BB21 hexon polypeptide (SEQ ID NO:7) or a BB24 hexon polypeptide (SEQ ID NO:8).

Embodiment 46 is an isolated hexon polypeptide comprising an amino acid sequence selected from a Ptr01 hexon polypeptide (SEQ ID NO:10) or a Ptr13 hexon polypeptide (SEQ ID NO:12).

Embodiment 47 is an isolated fiber polypeptide, wherein the fiber polypeptide has at least 98% identity to amino acids 6-375 of SEQ ID NO:2.

Embodiment 48 is the isolated fiber polypeptide of embodiment 47, wherein the fiber polypeptide has at least 99% identity to amino acids 6-375 of SEQ ID NO:2.

Embodiment 49 is an isolated fiber polypeptide, wherein the fiber polypeptide has at least 98% identity to SEQ ID NO:2.

Embodiment 50 is the isolated fiber polypeptide of embodiment 49, wherein the fiber polypeptide has at least 99% identity to SEQ ID NO:2.

Embodiment 51 is the isolated fiber polypeptide of embodiment 49, wherein the fiber polypeptide comprises an amino acid sequence selected from a BB21 fiber polypeptide (SEQ ID NO:2), a BB21 fiber variant polypeptide (SEQ ID NO:3), or a BB24 fiber polypeptide (SEQ ID NO:4).

Embodiment 52 is the vaccine of embodiment 41 for inducing an immune response in a subject in need thereof.

Embodiment 53 is use of the vaccine of embodiment 41 for the manufacture of a medicament for inducing an immune response in a subject in need thereof.

Embodiment 54 is an adenoviral vector, wherein the adenoviral vector comprises a nucleic acid sequence selected from the group consisting of SEQ ID NO:40, SEQ ID NO:41, SEQ ID NO:48, SEQ ID NO:49, SEQ ID NO:54, SEQ ID NO:55, SEQ ID NO:58, and SEQ ID NO:59.

Embodiment 55 is the adenoviral vector of embodiment 54, wherein the adenoviral vector comprises a nucleic acid sequence of SEQ ID NO:40.

Embodiment 56 is the adenoviral vector of embodiment 54, wherein the adenoviral vector comprises a nucleic acid sequence of SEQ ID NO:41.

Embodiment 57 is the adenoviral vector of embodiment 54, wherein the adenoviral vector comprises a nucleic acid sequence of SEQ ID NO:48.

Embodiment 58 is the adenoviral vector of embodiment 54, wherein the adenoviral vector comprises a nucleic acid sequence of SEQ ID NO:49.

Embodiment 59 is the adenoviral vector of embodiment 54, wherein the adenoviral vector comprises a nucleic acid sequence of SEQ ID NO:54.

Embodiment 60 is the adenoviral vector of embodiment 54, wherein the adenoviral vector comprises a nucleic acid sequence of SEQ ID NO:55.

Embodiment 61 is the adenoviral vector of embodiment 54, wherein the adenoviral vector comprises a nucleic acid sequence of SEQ ID NO:58.

Embodiment 62 is the adenoviral vector of embodiment 54, wherein the adenoviral vector comprises a nucleic acid sequence of SEQ ID NO:59.

EXAMPLES

Example 1: Generation of E1- and E3-Deleted Vectors Based on Novel Adenovirus Isolates BB21 and BB24

Figure 15:
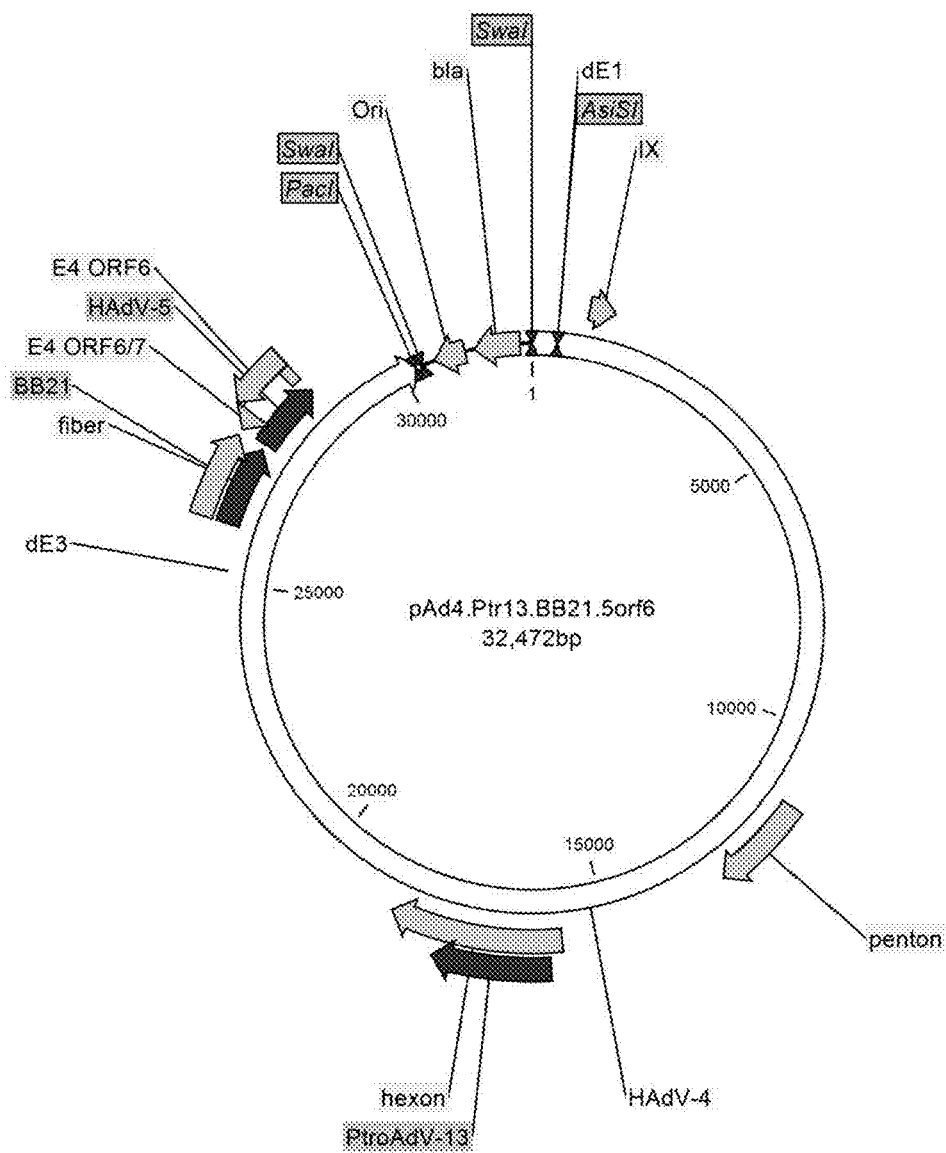
FIG. 15 shows a schematic of the plasmid pAd4.Ptr13.BB21.5orf6 (SEQ ID NO:24).

Two novel chimpanzee adenovirus isolates, BB21 (also designated JAd2-WT) and BB24 (also designated JAd3-WT), were identified and sequenced. The chimpanzee adenovirus isolates were found to phylogenetically belong to the human adenovirus species E (HAdV-E) group. The full genome nucleotide sequence of BB21 and BB24 were determined to be SEQ ID NO:13 and SEQ ID NO:14, respectively. The BB21 hexon and fiber polypeptide sequences were determined to be SEQ ID NOs:7 and 2, respectively. The BB24 hexon and fiber polypeptide sequences were determined to be SEQ ID NOs:8 and 4, respectively. An alignment of the BB21 and BB24 fiber polypeptide sequences is provided in FIG. 15.

Figure 9:
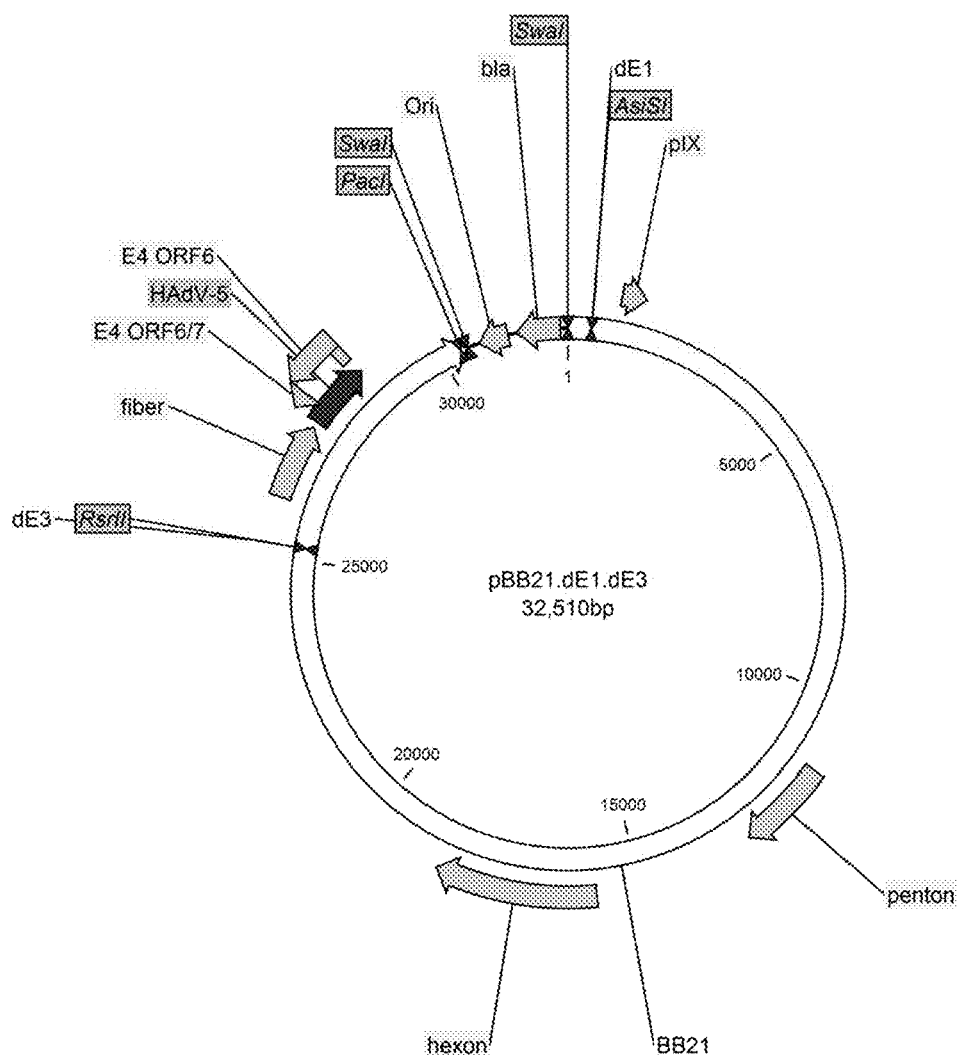
FIG. 9 shows a schematic of the plasmid pBB21.dE1.dE3 (SEQ ID NO:15).
Figure 10:
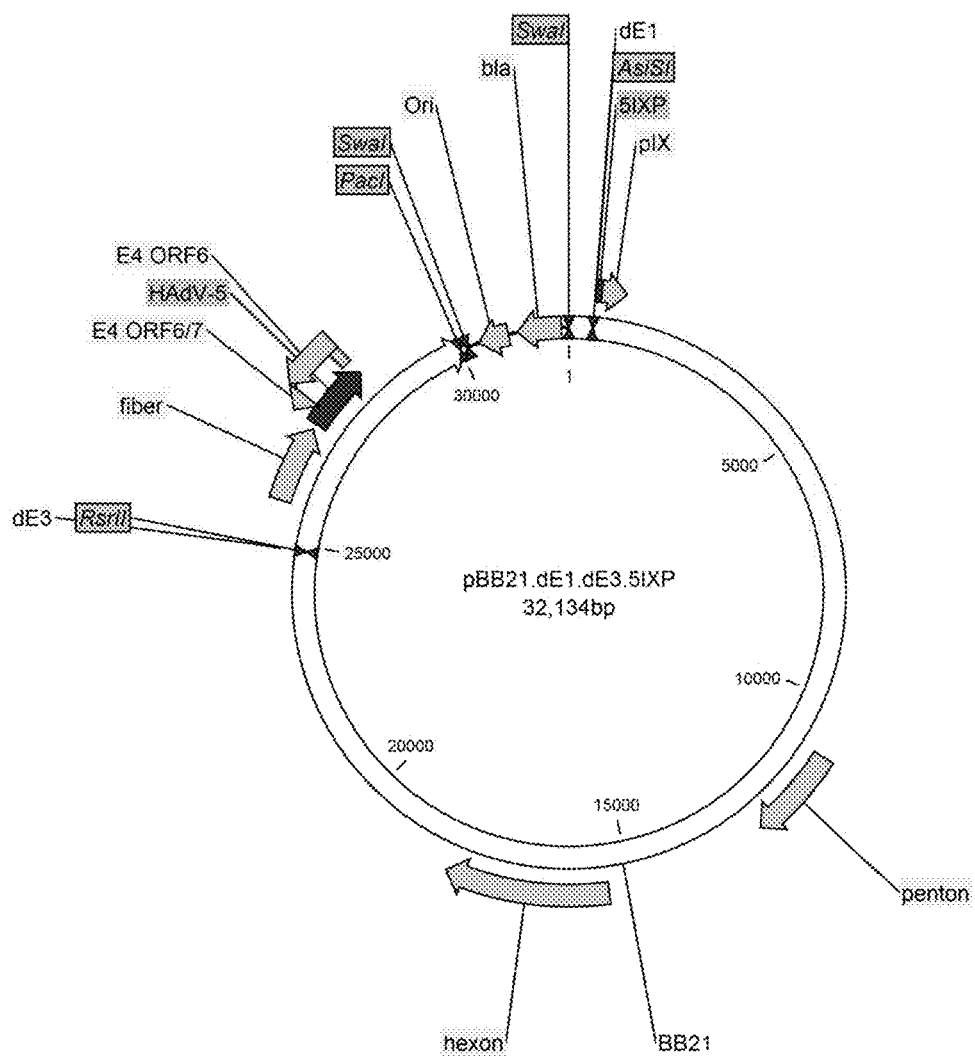
FIG. 10 shows a schematic of the plasmid pBB21.dE1.dE3.5IXP (SEQ ID NO:16).
Figure 11:
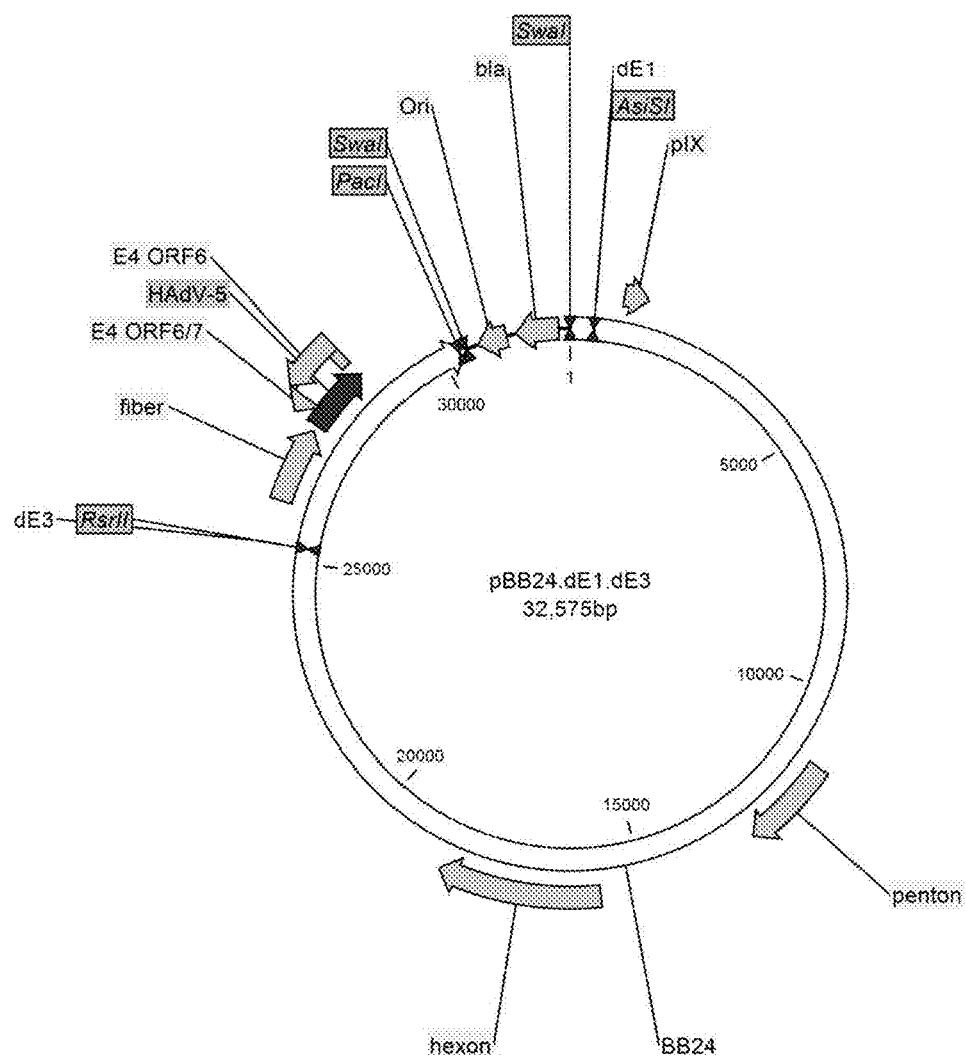
FIG. 11 shows a schematic of the plasmid pBB24.dE1.dE3 (SEQ ID NO:17).
Figure 12:
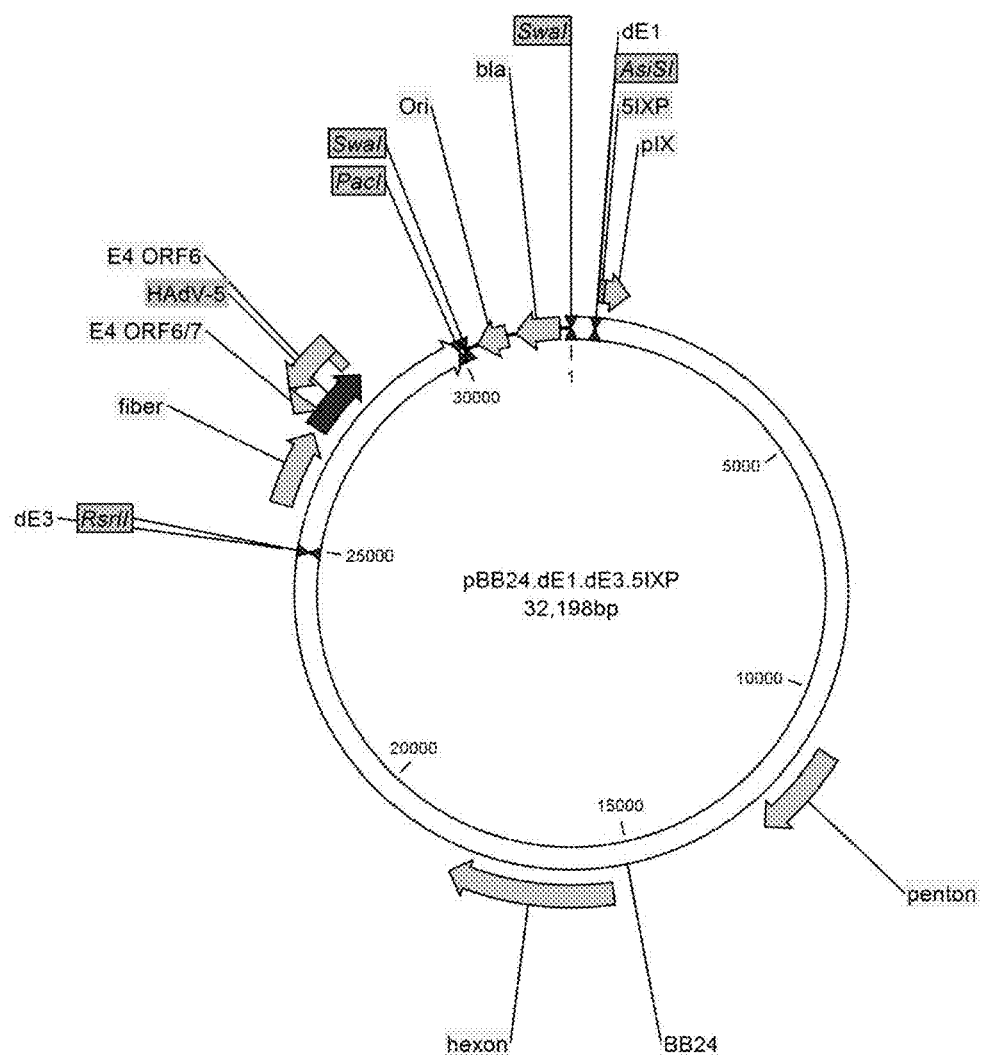
FIG. 12 shows a schematic of the plasmid pBB24.dE1.dE3.5IXP (SEQ ID NO:18).

Description of the Single Plasmid Systems Used for the Generation of BB21- and BB24-Based Ad Vectors pBB21.dE1.dE3 (SEQ ID NO:15; FIG. 9), pBB21.dE1.dE3.5IXP (SEQ ID NO:16; FIG. 10), pBB24.dE1.dE3 (SEQ ID NO:17; FIG. 11), and pBB24.dE1.dE3.5IXP (SEQ ID NO:18; FIG. 12) are plasmids carrying full-length, E1- and E3-deleted adenoviral vector genomes based on isolates BB21 and BB24. The Ad vector genome sequences contained within these plasmids are set forth in SEQ ID NO:28, SEQ ID NO:29, SEQ ID NO:30, and SEQ ID NO:31, respectively. Within each of these plasmids, the adenoviral vector genome is flanked by two SwaI restriction enzyme sites (i.e. one SwaI site is located at either end of the vector genome). These SwaI sites are meant to facilitate excision of the Ad vector genome from the plasmid backbone prior to viral rescue by transfection of suitable E1-complementing cells (such as HEK293, 911, and PER.C6 cells). The Ad vector genomes comprised by these plasmids further carry certain restriction enzyme sites introduced in the location of the E1 deletion, in the E3 deletion, and adjacent to the right inverted terminal repeat (RITR). These restriction enzyme sites were selected to be unique in the context of the complete Ad genome plasmids. They represent "transgene insertion sites" that allow for the facile construction, by standard molecular cloning techniques, of Ad vectors carrying one or more transgene expression cassettes inserted at any of said respective locations or any combinations thereof. Ad vector designs and plasmid constructions are described in more detail in the sections below.

BB21- and BB24-Based Ad Vector Genome Design

The BB21- and BB24-based Ad vector genomes were each designed to comprise an E1 deletion, an E3 deletion, different transgene insertion sites, and a replacement of the native E4 open reading frame (orf) 6 and orf6/7 with that of human adenovirus-5 (HAdV-5). The E1 region of each adenovirus was deleted and replaced with a transgene insertion site comprising an AsiSI restriction enzyme site sequence. The E3 region of each adenovirus was deleted and replaced with a transgene insertion site comprising an RsrII restriction enzyme site sequence. Another transgene insertion site was created by insertion of a PacI restriction enzyme site sequence adjacent to the inverted terminal repeat (ITR) of each adenovirus. The BB21 and BB24 sequences comprising E4 orf6 and orf6/7 coding sequences were replaced by SEQ ID NO:32 and SEQ ID NO:42, respectively. These replacing sequences comprise the E4 orf6 and orf6/7 coding sequences of human adenovirus-5 (HAdV-5) (base pairs 32914-34077 of GenBank sequence AC_000008) modified to carry one silent mutation eliminating a certain AseI site (for cloning purposes).

Two types of E1 region deletions were designed and constructed. The BB21- and BB24-based Ad vector genomes respectively comprised by pBB21.dE1.dE3 and pBB24.dE1.dE3 carry an E1 region deletion corresponding to removal of, respectively, nucleotides 456 to 3027 of SEQ ID NO:13 and nucleotides 457 to 3025 of SEQ ID NO:14. By contrast, the BB21- and BB24-based Ad vector genomes respectively comprised by pBB21.dE1.dE3.5IXP and pBB24.dE1.dE3.5IXP carry a larger E1 region-comprising sequence deletion that removes all the E1 coding sequences of BB21 or BB24 (i.e. nucleotides 456 to 3418 of SEQ ID NO:13 or nucleotides 457 to 3420 of SEQ ID NO:14, respectively). These latter two Ad vector genomes were additionally designed to carry a replacement of the non-coding sequence stretch between E1B 55K and pIX coding sequences by that of HAdV-5 (i.e. sequences corresponding to nucleotides 3419 to 3502 of SEQ ID NO:13 or 3421 to 3504 of SEQ ID NO:14 were replaced by nucleotides 3510-3608 of GenBank AC_000008 (i.e. by SEQ ID NO:27)).

Construction of Single Plasmids Comprising BB21-Based Ad Vector Genomes pBB21.dE1.dE3 (SEQ ID NO:15) was constructed by several steps of gene synthesis (performed by GenScript; Piscataway, N.J.) and standard molecular cloning procedures. First, a 3576 bp DNA fragment (SEQ ID NO:33) containing the right end of the desired Ad vector genome (i.e. harboring the aforementioned E3 deletion, partial E4 sequence replacement, and transgene insertion site adjacent to the RITR) was synthesized and ligated, as an EcoRI-AseI restriction fragment, into EcoRI- and NdeI-digested pBR322 (GenBank accession number—J01749.1), leading to BB21 intermediate plasmid 1. Second, a 4256 bp fragment (SEQ ID NO:34) containing the left end of the desired Ad vector genome (i.e. harboring the aforementioned E1 deletion) was synthesized and ligated, as an SnaBI-EcoRI restriction fragment, into ZraI- and EcoRI-digested BB21 intermediate plasmid 1, leading to BB21 intermediate plasmid 2. Third, a 4077 bp fragment (SEQ ID NO:35) containing a middle Ad vector genome fragment was synthesized and ligated as a EcoRI-HpaI restriction fragment into EcoRI- and HpaI-digested BB21 intermediate plasmid 2, leading to BB21 intermediate plasmid 3 (SEQ ID NO:36). Fourth, the 18815 bp AbsI-EcoRI restriction fragment of the BB21 viral genome (SEQ ID NO:13) was ligated into AbsI- and EcoRI-digested BB21 intermediate plasmid 3, leading to the final plasmid pBB21.dE1.dE3 (SEQ ID NO:15).

pBB21.dE1.dE3.5IXP (SEQ ID NO:16) was constructed in the same way as pBB21.dE1.dE3 except that abovementioned BB21 intermediate plasmid 3 (SEQ ID NO:36) was first modified to contain the desired E1 deletion and Ad5 pIX promoter insertion. This was done by synthesis of a 224 bp fragment (SEQ ID NO:37) that was subsequently ligated as an AsiSI-FseI restriction fragment into AsiSI- and FseI-digested BB21 intermediate plasmid 3.

pBB21.FLuc (SEQ ID NO:38) and pBB21.RSVF-2A-GLuc (SEQ ID NO:39) are pBB21.dE1.dE3-derived plasmids that each harbor a BB21-based Ad vector genome equipped with a transgene expression cassette inserted at the location of the E1 deletion. The Ad vector genome sequences carried within these plasmids are set forth in SEQ ID NO:40 and SEQ ID NO:41, respectively. pBB21.FLuc carries a transgene expression cassette for firefly luciferase (FLuc). This cassette is driven by the cytomegalovirus major immediate early promoter (i.e. the "CMV promoter") and contains an SV40-derived polyadenylation signal. pBB21.RSVF-2A-Gluc carries a transgene expression cassette for "RSV-$F_{A2}$-2A-GLuc" (RSVF-2A-GLuc), which is a chimeric protein composed of the respiratory syncytial virus strain A2 fusion glycoprotein, a foot-and-mouth-disease virus 2A peptide, and Gaussia luciferase (GLuc). Like the FLuc cassette, this cassette is driven by a CMV promoter and carries an SV40 polyadenlyation signal. In addition, this cassette contains within its 5'untranslated region a sequence comprising intron 2 of the human Apolipoprotein A1 gene. The Fluc and RSVF-2A-GLuc expression cassettes were each constructed by several standard gene synthesis and molecular cloning steps after which they were ligated into the unique AsiSI restriction enzyme site of pBB21.dE1.dE3, generating pBB21.FLuc and pBB21.RSVF-2A-Gluc, respectively.

Construction of Single Plasmids Comprising BB24-Based Ad Vector Genomes pBB24.dE1.dE3 (SEQ ID NO:17) was constructed by several steps of gene synthesis (performed by GenScript) and standard molecular cloning procedures. First, a 8144 bp DNA fragment (SEQ ID NO:43) containing the left and rights ends of the desired Ad vector genome (i.e. harboring the aforementioned E1 deletion, E3 deletion, partial E4 sequence replacement, and transgene insertion site adjacent to the RITR) was synthesized and ligated, as an MfeI-AseI restriction fragment, into EcoRI- and NdeI-digested pBR322 (GenBank accession number J01749.1), leading to BB24 intermediate plasmid 1 (SEQ ID NO:44). Second, the 22482 bp NdeI-EcoRI restriction fragment of the BB24 viral genome (SEQ ID NO:14) was ligated into NdeI- and EcoRI-digested BB24 intermediate plasmid 1, leading to the final plasmid pBB24.dE1.dE3.

pBB24.dE1.dE3.5IXP (SEQ ID NO:18) was constructed in a similar manner. First, the abovementioned BB24 intermediate plasmid 1 (SEQ ID NO:44) was modified to carry the desired E1 deletion and Ad5 pIX promoter insertion. This was done by synthesis of a 2671 bp fragment (SEQ ID NO:45) that was subsequently ligated as an AsiSI-EcoRI restriction fragment into AsiSI- and EcoRI-digested BB24 intermediate plasmid 1. Second, the 19470 bp XbaI-EcoRI restriction fragment of the BB24 viral genome (SEQ ID NO:14) was ligated into the modified plasmid (digested with XbaI and EcoRI).

pBB24.FLuc (SEQ ID NO:46) and pBB24.RSVF-2A-GLuc (SEQ ID NO:47) are pBB24.dE1.dE3-derived plasmids that each contain a BB24-based Ad vector genome equipped with a transgene expression cassette inserted at the location of the E1 deletion. The Ad vector genome sequences carried within these plasmids are set forth in SEQ ID NO:48 and SEQ ID NO:49, respectively. pBB24.FLuc carries the same FLuc expression cassette as described herein for pBB21.FLuc. pBB24.RSVF-2A-GLuc carries the same RSVF-2A-GLuc expression cassette as described herein for pBB21.RSVF-2A-GLuc. These two cassettes were each constructed by several standard gene synthesis and molecular cloning steps after which they were ligated into the unique AsiSI restriction enzyme site of pBB24.dE1.dE3, generating pBB24.FLuc and pBB24.RSVF-2A-GLuc, respectively.

Generation and Production of BB21- and BB24-Based Adenoviral Vectors

Adenoviral vectors BB21.FLuc (also designated JAd2NVT003), BB21.RSVF-2A-GLuc (also designated JAd2NVT001), BB24.FLuc (also designated JAd3NVT003), and BB24.RSVF-2A-GLuc (also designated JAd3NVT001), which respectively comprise adenoviral vector genome sequences SEQ ID NO:40, SEQ ID NO:41, SEQ ID NO:48, and SEQ ID NO:49, were generated by transfection of the corresponding Ad vector genome plasmids (i.e. pBB21.FLuc, pBB21.RSVF-2A-GLuc, pBB24.FLluc, and pBB24.RSVF-2A-GLuc) into E1-complementing PER.C6 cells. Prior to transfection into PER.C6 cells, which were grown as adherent cell cultures in Dulbecco's modified Eagle's medium (DMEM) supplemented with 10% fetal bovine serum (FBS) and 10 mM $MgCl_2$, the Ad vector genome plasmids were digested with SwaI to release the respective adenoviral vector genomes from the plasmid. The transfections were performed according to standard procedures using Lipofectamine transfection reagent (Invitrogen; Carlsbad, Calif.). After harvesting of the viral rescue transfections, the viruses were further amplified by several successive infection rounds on PER.C6 cell cultures. The viruses were purified from crude viral harvests using a two-step cesium chloride (CsCl) density gradient ultracentrifugation procedure as described before (Havenga et al., "Novel replication-incompetent adenoviral B-group vectors: high vector stability and yield in PER.C6 cells," J. Gen. Virol. 87(8):2135-43 (2006)). Viral particle (VP) titers were measured by a spectrophotometry-based procedure described previously (Maizel et al., "The polypeptides of adenovirus: I. Evidence for multiple protein components in the virion and a comparison of types 2, 7A, and 12," Virology, 36(1):115-25 (1968)).

Example 2: Generation of E1- and E3-Deleted Vectors Based on the HAdV-4 Harboring Hexon and Fiber Sequences from Ape Adenoviruses In order to create replication-incompetent adenoviral vectors based on human adenovirus type 4 (HAdV-4) that are modified in hexon, or hexon and fiber sequences, plasmids were constructed carrying a complete HAdV-4 vector genome harboring the E1 and E3 deletions, transgene insertions, and hexon and/or fiber replacements as described below. Transgene expression cassettes were inserted into the E1 deletion of the vector. Transfection of the plasmids into E1 complementing cell lines such as HEK 293 or PER.C6 resulted in rescue of the HAdV-4 based vectors wherein the capsid proteins (hexon, or hexon and fiber) had been replaced by heterologous sequences derived from certain ape adenovirus isolates. The design and construction of the Ad vector plasmids is described in the following sections.

Design and Construction of Single Plasmids Comprising HAdV-4-Based Ad Vector Genomes The complete sequence of the HAdV-4 isolate used for vector design and construction (35990 bp) was previously determined (SEQ ID NO:19).

A single plasmid carrying a HAdV-4 based vector genome (harboring deletions to render it replication-incompetent, as well as to create space for the insertion of foreign transgene cassettes) was created using standard molecular biology and DNA cloning techniques. Briefly, DNA fragments comprising the left and right ends of the desired HAdV-4-based Ad vector were synthesized at GenScript and cloned into pBR322. Subsequently the missing middle portion of the HAdV-4 genome, a HindIII-HindIII restriction fragment of approximately 19 kbp, was obtained from purified wild type HAdV-4 genomic DNA (by restriction enzyme digestion) and then ligated into the left and right end-containing pBR322-based plasmid. This resulted in the generation of plasmid pAd4.dE1.dE3. This plasmid carries an E1- and E3-deleted HAdV-4-based Ad vector genome flanked by SwaI sites. These SwaI sites allow for excision of the vector genome from the plasmid for rescue of the adenoviral vector by transfection of an E1-complementing cell line, such as a PER.C6 or HEK293 cell line. At the location of the E1 deletion, the plasmid carries a transgene insertion site comprised by an AsiSI restriction enzyme site. Another transgene insertion site, comprised by a PacI site, is located adjacent to the right inverted terminal repeat.

Figure 13:
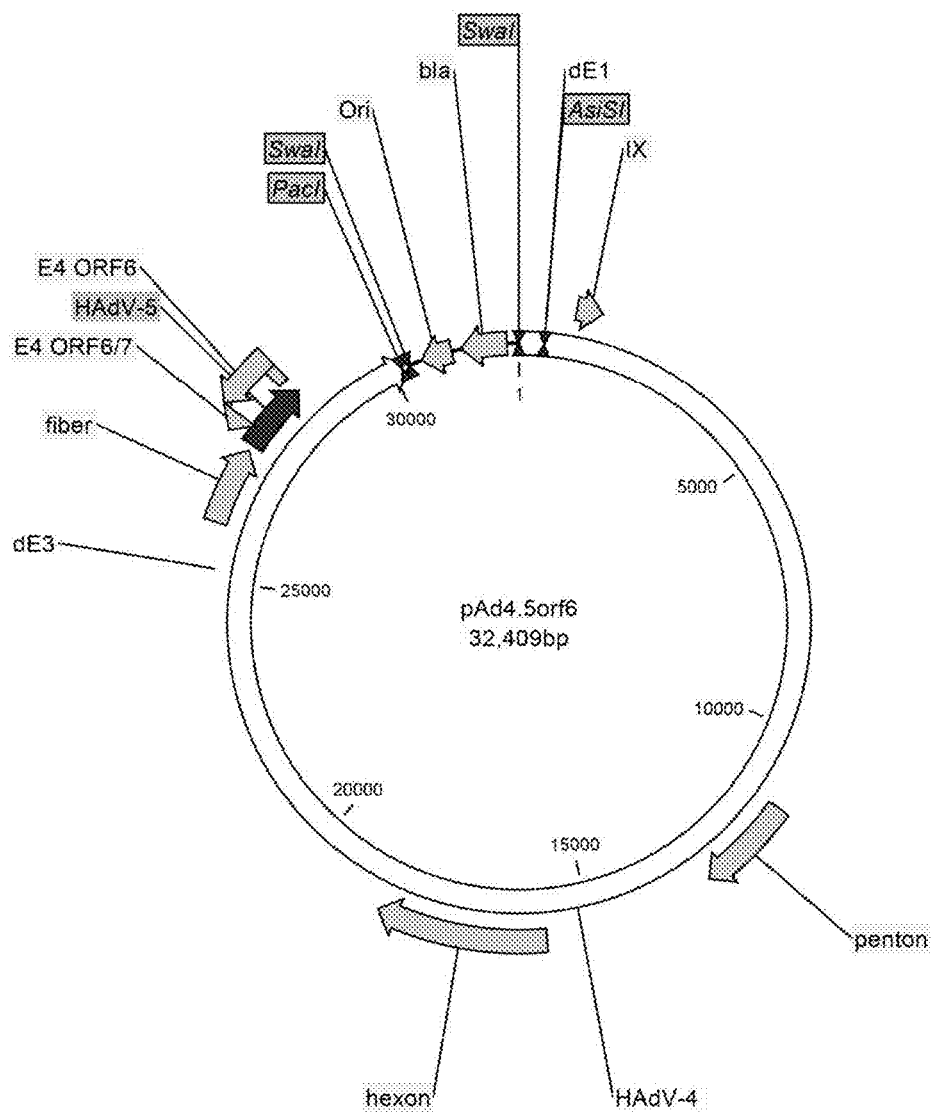
FIG. 13 shows a schematic of the plasmid pAd4.5orf6 (SEQ ID NO:20).

An E4 region-modified version of pAd4.dE1.dE3, pAd4.5orf6 (SEQ ID NO:20; FIG. 13) was also made. While pAd4.dE1.dE3 was created to contain the native HAdV-4 E4 sequence, pAd4.5orf6 was created to contain a modified E4 region in which nucleotides 33018-34165 of the native HAdV-4 sequence were replaced with a sequence containing E4 orf6 and orf6/7 sequences from HAdV-5 (i.e., nucleotides 32914-34077 of HAdV-5 GenBank Sequence AC_000008 (SEQ ID NO:50). The Ad vector genome sequence carried within pAd4.5orf6 set forth in SEQ ID NO:51. pAd4.5orf6 was generated by excision and replacement, using standard cloning techniques, of a 2.9 kb PsiI-PacI fragment of pAd4.dE1.dE3 by a synthesized sequence (generated by GenScript) carrying the described modification. Apart from the modified E4 region, the plasmids pAd4.dE1.dE3 and pAd4.5orf6 are the same. A map of pAd4.5orf6 is shown in FIG. 12. The E1 and E3 deletions, as well as regions coding for hexon and fiber are indicated.

Both HAdV-4-based vector versions could be rescued upon transfection of the respective plasmids (i.e. pAd4.dE1.dE3 and pAd4.5orf6) in suitable E1-complementing cells (like HEK293 and PER.C6). However, the use of the E4 orf6-containing sequence from HAdV-5 was found to improve vector yields and efficiency of production. Previously, an analogous replacement in a HAdV-35-based vector showed similar results (Havenga et al., "Novel replication-incompetent adenoviral B-group vectors: high vector stability and yield in PER.C6 cells," J. Gen. Virol. 87(8):2135-43 (2006)).

pAd4.dE1.dE3 and pAd4.5orf6 each carry within the Ad vector genome a unique AsiSI restriction site at the location of the E1 deletion and a unique PacI restriction site adjacent to the right inverted terminal repeat. These sites allow for insertion of transgene expression cassettes at the respective locations of the Ad vector genome by standard cloning techniques. For example, one or more of such cassettes may be inserted at one or both of these locations.

pAd4.FLuc and pAd4.RSVF-2A-GLuc are transgene expression cassette-containing versions of pAd4.5orf6, respectively carrying transgene cassettes encoding firefly luciferase (FLuc) and a fusion protein comprising the respiratory syncytial virus A2 fusion glycoprotein, a foot-and-mouth-disease virus-derived 2A peptide, and *Gaussia* luciferase (RSVF-2A-GLuc). They were constructed by insertion of the respective cassettes into the AsiSI site of pAd4.5orf6 by standard cloning techniques. The two transgene cassettes are the same as those employed in Example 1 in the context of BB21- and BB24-based adenoviral vectors.

Figure 14:
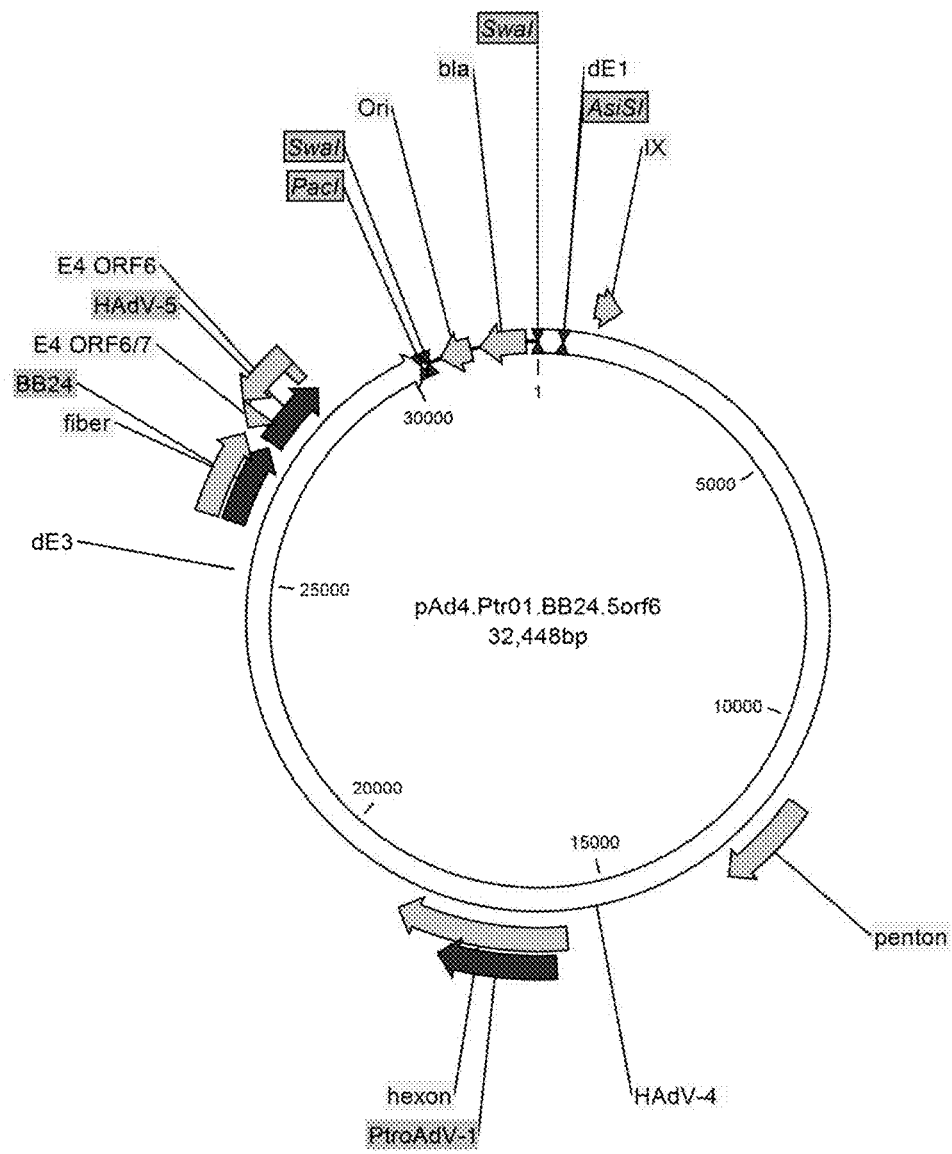
FIG. 14 shows a schematic of the plasmid pAd4.Ptr01.BB24.5orf6 (SEQ ID NO:23).

Design and Construction of Single Plasmids Comprising HAdV-4 Based Vectors Carrying Hexon and Fiber Sequence Replacements HAdV-4-based vector genome plasmids were constructed in which hexon and fiber coding sequences were replaced by those of certain chimpanzee adenovirus isolates that like HAdV-4 have been allocated to human Ad species E. Adenovirus isolates that served as hexon sequence donor for these constructions are PtroAdV-1 and PtroAdV-13, for which partial hexon nucleotide sequence were previously deposited in GenBank (under JN163971 and JN163983, respectively). Fiber sequences used for the constructions came from the novel chimpanzee adenovirus isolates BB21 and BB24, which are described in Example 1 herein. Two different combinations of hexon and fiber sequence replacements were made (in context of HAdV-4-based vector genome plasmids): (1) PtroAdV-1 hexon nucleotide sequences were combined with nucleotide sequences encoding the BB24 fiber (SEQ ID NO:4) and (2) PtroAdV-13 hexon nucleotide sequences were combined with nucleotide sequences encoding a BB21 fiber variant (SEQ ID NO:3). Constructed plasmids carrying said first combination of hexon and fiber sequence replacements are pAd4.Ptr01.BB24.5orf6 (SEQ ID NO:23; FIG. 13), pAd4.Ptr01.BB24.5orf6.Fluc (SEQ ID NO:21), and pAd4.Ptr01.BB24.5orf6.RSVF-2A-Gluc (SEQ ID NO:52), which harbor the Ad vector genome sequences as set forth in SEQ ID NO:53, SEQ ID NO:54, and SEQ ID NO:55, respectively. Constructed plasmids carrying said second combination of hexon and fiber sequence replacements are pAd4.Ptr13.BB21.5orf6 (SEQ ID NO:24; FIG. 14), pAd4.Ptr13.BB21.5orf6.Fluc (SEQ ID NO:22), and pAd4.Ptr13.BB21.5orf6.RSVF-2A-Gluc (SEQ ID NO:56), which contain the Ad vector genome sequences as set forth in SEQ ID NO:57, SEQ ID NO:58, and SEQ ID NO:59, respectively.

Above hexon- and fiber-modified Ad vector genome plasmids were each constructed by standard gene synthesis and molecular cloning procedures. Sequence fragments comprising the respective modified hexon and fiber sequences were synthesized (by GenScript) and then subjected to sequential subcloning steps that together amounted to insertion of those sequences into pAd4.5orf6 (replacing therein the corresponding native HAdV-4 hexon- and fiber-comprising sequences). The resulting plasmids, pAd4.Ptr01.BB24.5orf6 and pAd4.Ptr13.BB21.5orf6, were subsequently equipped with the aforementioned expression cassettes for Fluc and RSVF-2A-Gluc by cloning of these cassettes into the unique AsiSI site of these plasmids (leading to construction of pAd4.Ptr01.BB24.5orf6.Fluc, pAd4.Ptr01.BB24.5orf6.RSVF-2A-Gluc, pAd4.Ptr13.BB21.5orf6.Fluc, and pAd4.Ptr13.BB21.5orf6.RSVF-2A-Gluc).

The hexon sequence replacements carried out herein resulted in the construction of chimeric hexon-encoding sequences "Ptr01" (SEQ ID NO:9) and "Ptr13" (SEQ ID NO:11). These sequences constitute HAdV-4 hexon genes wherein the hypervariable regions (HVRs)-encoding sequences were replaced by those of PtroAdV-1 and PtroAdV-13, respectively. The chimeric hexon polypeptides encoded by Ptr01 and Ptr13 are set forth in SEQ ID NO:10 and SEQ ID NO:12, respectively.

The fiber sequence replacements carried out herein entailed the replacement of the complete fiber-encoding sequence of HAdV-4 by sequences derived from fiber donor isolates BB21 and BB24, which are described in Example 1 herein. The replacement nucleotide sequences respectively encode a BB21 fiber variant (SEQ ID NO:3) and the BB24 fiber (SEQ ID NO:4). FIG. 16 displays a polypeptide alignment of these two fibers and BB21 fiber (SEQ ID NO:2).

Generation and Production of HAdV-4-Based Vectors Carrying Hexon and Fiber Sequence Replacements Adenoviral vectors Ad4Ptr01-BB24.FLuc (also designated Ad4C1NVT003), Ad4Ptr01-BB24.RSVF-2A-GLuc (also designated Ad4C1NVT001), Ad4Ptr13-BB21.FLuc (also designated Ad4C2NVT003), and Ad4Ptr13-BB21.RSVF-2A-GLuc (also designated Ad4C2NVT001), which respectively comprise adenoviral vector genome sequences SEQ ID NO:54, SEQ ID NO:55, SEQ ID NO:58, and SEQ ID NO:59, were generated by transfection into E1-complementing PER.C6 cells of SwaI-digested Ad vector genome plasmids pAd4.Ptr01.BB24.5orf6.FLuc, pAd4.Ptr01.BB24.5orf6.RSVF-2A-GLuc, pAd4.Ptr13.BB21.5orf6.FLuc, and pAd4.Ptr13.BB21.5orf6.RSVF-2A-GLuc, respectively. Likewise, the control adenoviral vectors Ad4.FLuc and Ad4.RSVF-2A-GLuc were generated from plasmids pAd4.FLuc and pAd4.RSVF-2A-GLuc, respectively. All transfections and subsequent vector amplifications, purifications, and titrations were done according to the same standard procedures as described for the BB21- and BB24-based vectors in Example 1 herein.

Assessment of Reduction in Anti-Adenovirus Neutralization Titer as a Consequence of Replacement of the HAdV-4 Hexon and Fiber Recombinant adenoviruses expressing firefly luciferase (with capsid protein hexon and fiber replacements, constructed as described) were used to determine whether replacing the capsid proteins, hexon and fiber, with homologous proteins from ape adenoviruses resulted in reduction in neutralization by human serum samples that harbored anti-HAdV-4 neutralizing activity.

Briefly, equal infectious-unit aliquots of crude viral stocks of the adenovirus to be tested were incubated with serial dilutions of a serum sample. The starting dilution used for these assays was 16-fold. Following the incubation period, the adenovirus aliquot was used to infect an indicator cell line, such as A549 cells where any adenovirus that was not neutralized as a result of the incubation with serum may infect the indicator cells. The virus transduced cells were then incubated overnight to allow for the expression of the firefly luciferase transgene. The neutralization titer of any serum sample harboring anti-adenovirus neutralizing activity was the minimum dilution of the serum that could achieve a 90% reduction in luciferase activity in the reporter cells compared to the adenovirus aliquot which was not incubated with serum.

The anti-adenovirus neutralization titer in 22 human serum samples (out of 79 samples tested) that were found to harbor Ad4.FLuc neutralizing antibodies was determined (Table 1). When compared to the neutralization titers of the same serum samples against the chimeric adenoviruses Ad4.Ptr01-BB24.FLuc and Ad4Ptr13-BB21.FLuc respectively, it was evident that there is a pronounced reduction in the anti-adenovirus neutralizing activity as a result of the capsid alterations in the hexon and fiber coding sequences. These results confirm that adenoviral hexon and fiber proteins contain important antigenic determinants of antibody-mediated adenovirus neutralization. They also illustrate that pre-existing anti-vector humoral immunity in humans against human adenovirus-based vectors (in this case Ad4.FLuc, a HAdV-4-based vector) could be circumvented by swapping the vector's hexon and fiber proteins by those of ape adenoviruses likely to have a low seroprevalence in human populations.

Taken together, Ad4Ptr01-BB24.FLuc and Ad4Ptr13-BB21.Fluc proved to be serologically distinct from their parental HAdV-4-based vector Ad4.Fluc. Moreover, there was either no (in case of Ad4Ptr01-BB24.FLuc) or only limited (in case of Ad4Ptr13-BB21.Fluc) neutralizing activity found against these two vectors in a panel of Ad4.Fluc-neutralizing human sera.

TABLE 1

Anti-adenovirus neutralization titers in human sera positive for anti-Ad4 neutralizing antibodies

| Serum # | Anti-AdV-4.FLuc titer | Anti-Ad4.Ptr01-BB24.FLuc titer | Anti-Ad4.Ptr13-BB21.FLuc titer |
|---|---|---|---|
| 1 | 726 | <16 | <16 |
| 2 | 328 | <16 | <16 |
| 3 | 285 | <16 | <16 |
| 4 | 252 | <16 | <16 |
| 5 | 116 | <16 | <16 |
| 6 | 102 | <16 | <16 |
| 7 | 86 | <16 | <16 |
| 8 | 78 | <16 | <16 |
| 9 | 70 | <16 | <16 |
| 10 | 63 | <16 | 110 |
| 11 | 59 | <16 | <16 |
| 12 | 58 | <16 | <16 |
| 13 | 53 | <16 | <16 |
| 14 | 50 | <16 | 47 |
| 15 | 48 | <16 | <16 |
| 16 | 42 | <16 | <16 |
| 17 | 40 | <16 | <16 |
| 18 | 33 | <16 | <16 |
| 19 | 32 | <16 | <16 |
| 20 | 31 | <16 | <16 |
| 21 | 29 | <16 | <16 |
| 22 | 22 | <16 | <16 |

<16 indicates there was no neutralization observed at lowest dilution of 16-fold Cellular and Humoral Immune Responses Induced by Novel Adenoviral Vectors Examples 3 to 8 describe experiments performed to assess the immunogenicity of four novel vectors generate herein, adenoviral vectors BB21, BB24, Ad4Ptr13-BB21, and Ad4Ptr01-BB24. In these experiments, the novel vectors were assessed for their abilities to induce humoral and cellular immune responses against vector-encoded (model) antigens in mice after intramuscular immunization. The vectors were tested using two different antigens: Firefly luciferase (FLuc) and RSV-$F_{A2}$-2A-GLuc (RSVF-2A-GLuc). RSVF-2A-GLuc is a chimeric protein composed of the respiratory syncytial virus strain A2 fusion glycoprotein, a foot-and-mouth-disease virus 2A peptide, and *Gaussia* luciferase (GLuc). Each vector was compared side-by-side with a benchmark vector based on human adenovirus type 26 (HAdV-26, also referred to herein as Ad26) carrying the same antigen-encoding transgene cassette. Immune responses against the respective antigens were measured using well-known immunological assays, such as enzyme-linked immunospot assay (ELISPOT), enzyme-linked immunosorbent assay (ELISA), and, in case of the RSVF-2A-GLuc antigen, a respiratory syncytial virus neutralization assay (VNA).

Example 3: Cellular Immune Responses Induced by BB21.FLuc and BB24.FLuc

Figure 1B:
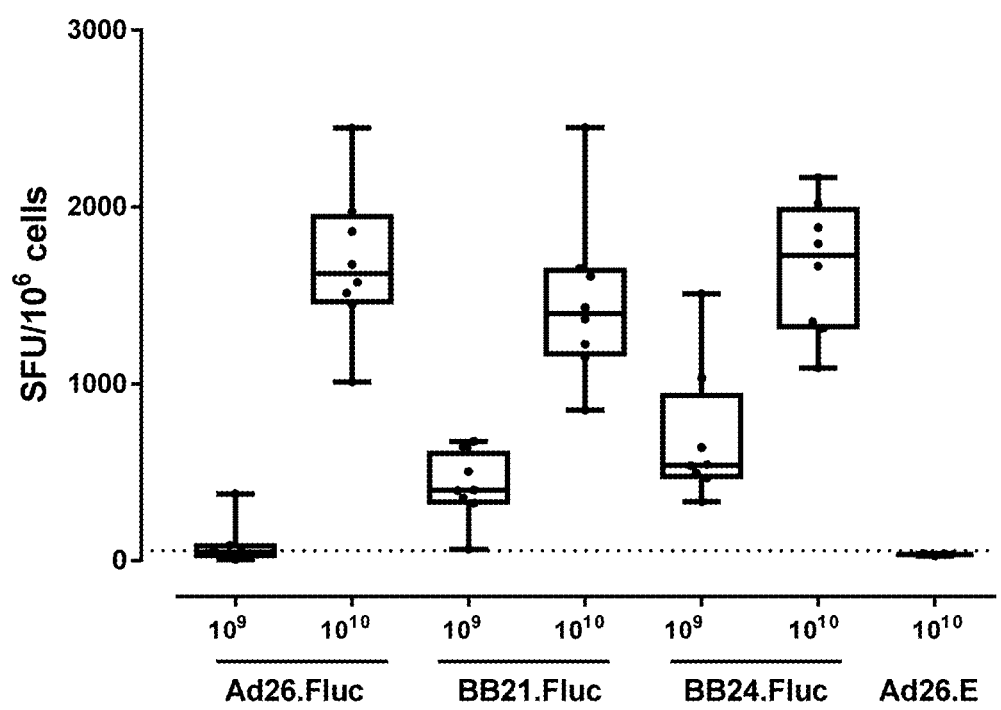

To evaluate the cellular immunogenicity of novel adenoviral vectors BB21 and BB24, Balb/C mice were immunized intramuscularly with Ad26.FLuc (positive control), BB21 or BB24 vectors expressing Firefly luciferase (i.e. BB21.FLuc or BB24.FLuc), or with an adenovector not encoding a transgene (Ad26 empty). Two vector doses were tested for administration: $10^9$ and $10^{10}$ viral particles (vp) per mouse. Two weeks after the immunization, mice were sacrificed and splenocytes were isolated (FIG. 1A). Cellular immune responses were determined by ex-vivo ELISPOT assay measuring the relative number of IFN-γ-secreting cells after overnight splenocyte stimulation with a 15mer overlapping FLuc peptide pool (FIG. 1B). The results show that at the higher-dose immunization ($10^{10}$), the cellular immune responses induced by BB21.FLuc and BB24.FLuc were about as high as the response seen for Ad26.FLuc. By contrast, at the lower-dose immunization ($10^9$), BB21.FLuc and BB24.FLuc both gave a higher response than Ad26.FLuc. Overall, the cellular immune responses induced by the FLuc-expressing recombinant BB21 and BB24 adenoviral vectors of the invention clearly indicate potent immunogenicity of these vectors in mice.

Example 4: Cellular Immune Responses Induced by Ad4Ptr13-BB21.FLuc

Figure 2:
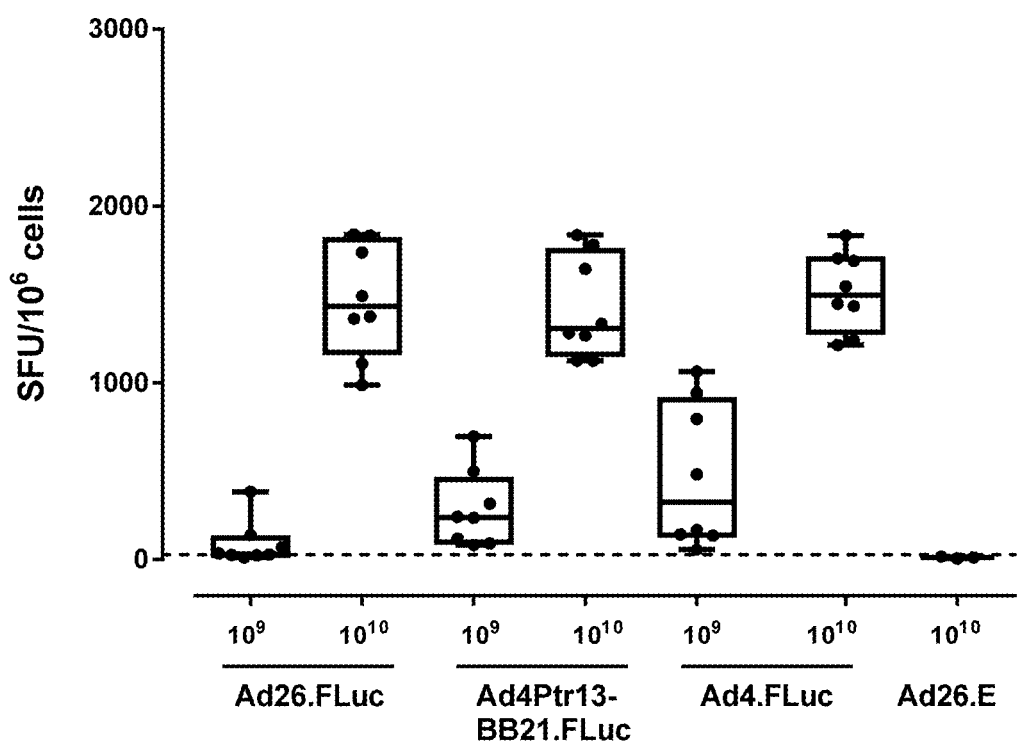
FIG. 2 shows cellular immune responses induced by Ad4Ptr13-BB21.FLuc and Ad4.FLuc. The graph shows the cellular immune responses induced by Ad26.FLuc, Ad4Ptr13-BB21.FLuc and Ad4.Fluc against the vector-encoded antigen (i.e. Fluc) as determined by IFN-γ ELISPOT analysis.

To evaluate the cellular immunogenicity of the novel engineered adenoviral vector Ad4Ptr13-BB21, Balb/C mice were immunized intramuscularly with Ad4Ptr13-BB21, Ad26 (positive control), or Ad4 (parental vector of Ad4Ptr13-BB21), each expressing Firefly luciferase (Fluc), or with an adenovector not encoding a transgene, Ad26 empty. Two vector doses were tested for administration: $10^9$ and $10^{10}$ viral particles (vp) per mouse. At two weeks after immunization, mice were sacrificed and splenocytes were isolated, according to the same experimental setup as used for BB21.Fluc and BB24.Fluc (FIG. 1A). Cellular immune responses were determined by ex-vivo ELISPOT assay measuring the relative number of IFN-γ-secreting cells after overnight splenocyte stimulation with a 15mer overlapping FLuc peptide pool (FIG. 2). The results show that at the higher-dose immunization ($10^{10}$), the cellular immune response induced by Ad4Ptr13-BB21.FLuc was about as high as that seen for the benchmark control vector Ad26.Fluc, while at the lower-dose immunization ($10^9$), Ad4Ptr13-BB21.FLuc gave a slightly higher response than Ad26.Fluc.

Overall, the cellular immune responses induced by the FLuc-expressing, novel engineered Ad4Ptr13-BB21 adenoviral vector, which comprises a BB21 fiber variant (SEQ ID NO:3), clearly indicate potent immunogenicity of this vector in mice.

Example 5: Cellular Immune Responses Induced by Ad4Ptr01-BB24.FLuc

Figure 3:
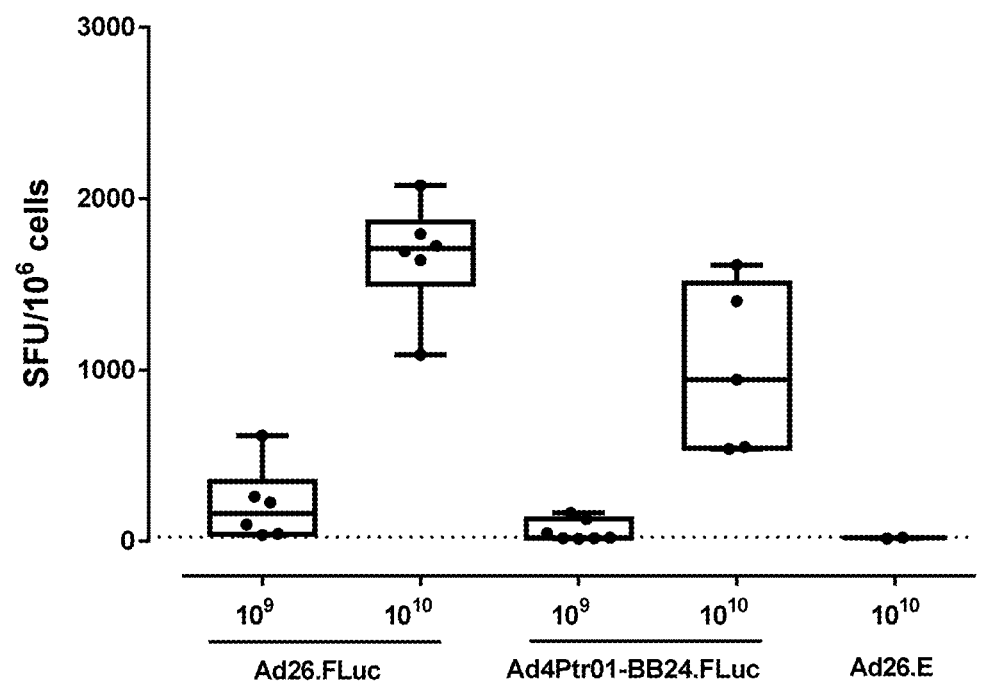
FIG. 3 shows cellular immune responses induced by Ad4Ptr01-BB24.FLuc. The graph shows the cellular immune responses induced by Ad26.FLuc and Ad4Ptr01-BB24.FLuc against the vector-encoded-antigen (i.e. Fluc) as determined by IFN-γ ELISPOT analysis.

To evaluate the cellular immunogenicity of the novel engineered adenoviral vector Ad4Ptr01-BB24.FLuc, Balb/C mice were immunized intramuscularly with Ad26.FLuc (positive control), Ad4Ptr01-BB24 expressing FLuc, or with an adenovector not encoding a transgene, Ad26 empty. Two doses were tested for administration: $10^9$ and $10^{10}$ viral particles (vp) per mouse. At two weeks after immunization, mice were sacrificed and splenocytes were isolated, according to the same experimental setup as used for BB21.Fluc and BB24.Fluc (FIG. 1A). Cellular immune responses were determined by ex-vivo ELISPOT assay measuring the relative number of IFN-γ-secreting cells after overnight splenocyte stimulation with a 15mer overlapping FLuc peptide pool (FIG. 3). The results show that, at the higher dose, Ad4Ptr01-BB24.FLuc clearly induced cellular immune responses against the encoded antigen, with readouts close to, but somewhat lower than, those seen for the positive control vector Ad26.Fluc.

Overall, the cellular immune responses induced by the FLuc-expressing, novel engineered Ad4Ptr01-BB24 adenoviral vector, which comprises the BB24 fiber (SEQ ID NO:4), clearly indicate immunogenicity of this vector in mice.

Example 6: Cellular and Humoral Immune Responses Induced by BB21.RSVF-2A-GLuc

Figure 4A:
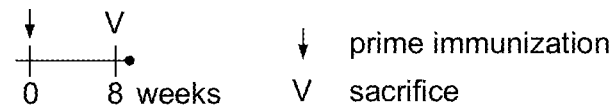
FIG. 4A-FIG. 4D show cellular and humoral immune responses induced by BB21.RSVF-2A-GLuc.

The immunogenicity of novel adenoviral vector BB21 was further evaluated using RSV-$F_{A2}$-2A-GLuc (RSVF-2A-GLuc) as a vector-encoded (model) vaccine antigen. Balb/C mice were immunized intramuscularly with Ad26.RSVF-2A-GLuc (positive control) or BB21.RSVF-2A-GLuc (both at $10^8$, $10^9$ and $10^{10}$ viral particles per mouse), or with Ad26.FLuc or BB21.FLuc (both at $10^{10}$ viral particles per mouse). Mice were sacrificed at eight weeks and blood samples and splenocytes were collected (FIG. 4A). Different immune parameters were assessed as described below.

Figure 4B:
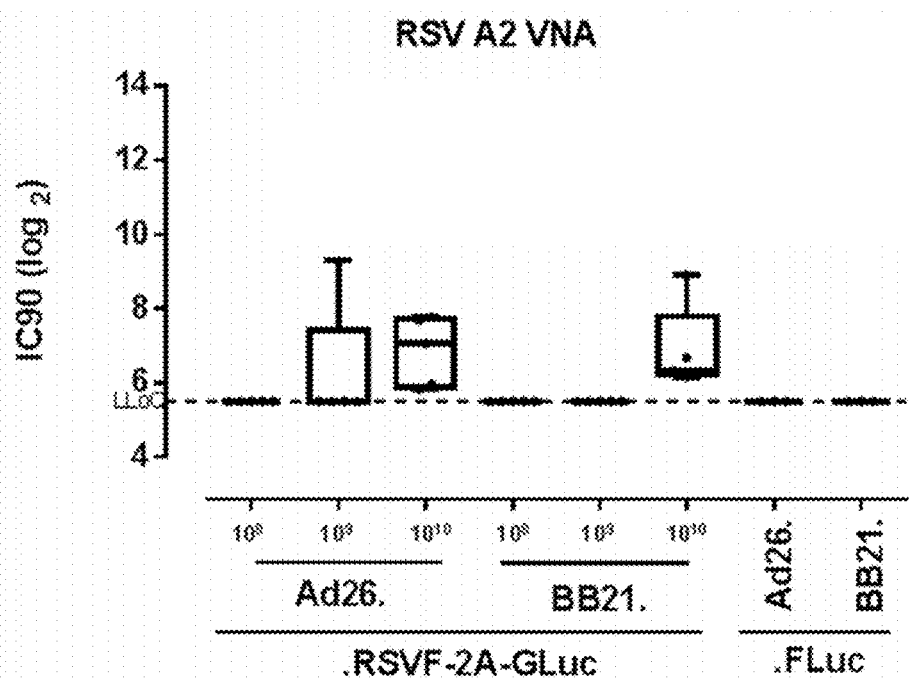

A virus neutralization assay was performed in order to assess the capacity of BB21.RSVF-2A-Gluc to elicit respiratory syncytial virus-neutralizing-antibodies. FIG. 4B depicts the respiratory syncytial virus strain A2 (RSV A2) VNA titers measured for sera samples collected eight weeks after immunization. Each dot represents one mouse, the bars represent the group mean, and the dotted line corresponds to the lower limit of quantification (LLOQ=6.88; mean endpoint titer of linearity samples). The results show that the $10^{10}$ vp-dose immunizations with BB21.RSVF-2A-Gluc gave rise to RSV A2 neutralization titers in the same range as those found for the benchmark Ad26 vector encoding the same antigen.

Figure 4C:
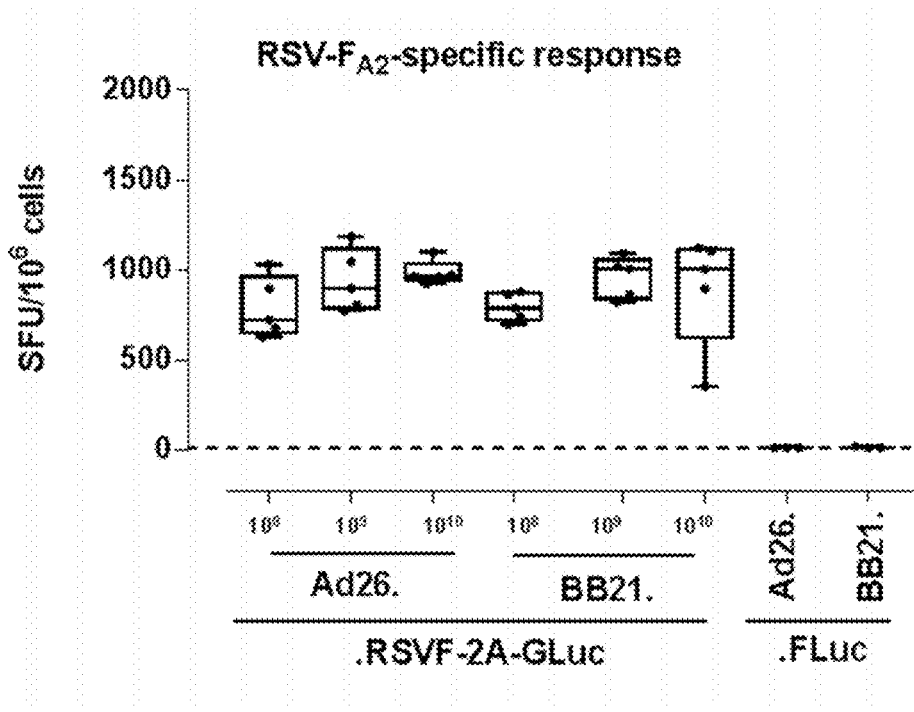

Induction of cellular immunity against the vector-encoded antigen was evaluated by an RSV-$F_{A2}$-specific ELISPOT assay. To this end, eight weeks after immunization, splenocytes from immunized mice were isolated and stimulated overnight with 15mer overlapping peptides spanning the RSV-$F_{A2}$ protein and cellular immune responses were determined by ex-vivo ELISPOT assay measuring the relative number of IFN-γ-secreting cells. The data show that the antigen-specific cellular immune responses elicited by BB21.RSVF-2A-GLuc were dose-dependent and, per dose, similar in magnitude to those induced by the benchmark vector, Ad26.RSVF-2A-GLuc (FIG. 4C). As expected, no RSV-$F_{A2}$-specific responses were measured from splenocytes of mice immunized with adenovectors encoding Firefly luciferase.

Figure 4D:
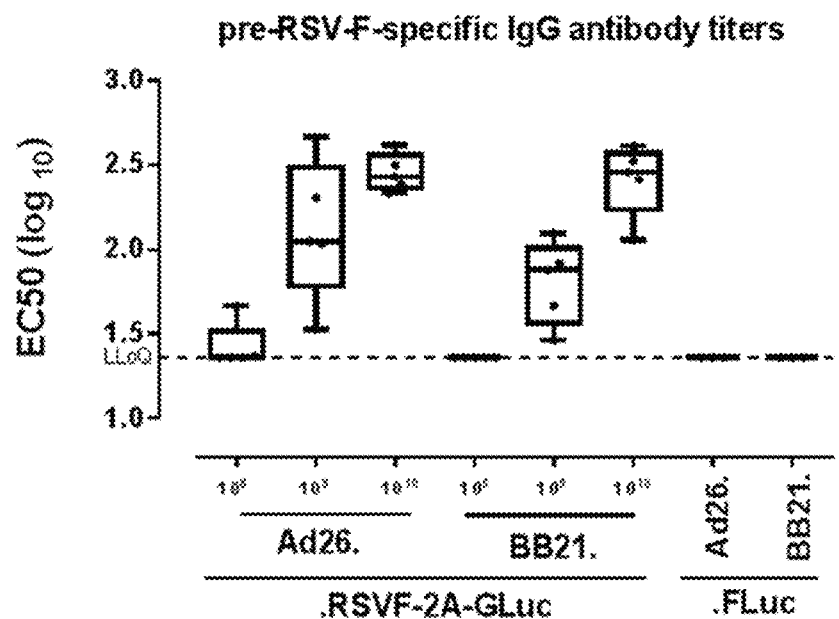

The ability of the RSVF-2A-GLuc-expressing vectors to elicit RSV-$F_{A2}$-specific IgG antibodies was assessed by ELISA. Sera collected 8 weeks post-immunization from the mice immunized with Ad26 or BB21 vectors expressing RSVF-2A-GLuc or Firefly luciferase were tested in an anti-RSV $F_{A2}$ IgG antibody ELISA. Specifically, this ELISA detects IgG antibodies capable of binding to a recombinant stable pre-fusion RSV-$F_{A2}$ protein (pre-RSV-F). The results show that BB21.RSVF-2A-GLuc dose-dependently elicited pre-RSV-F-specific IgG antibody titers similar to those induced by Ad26.RSVF-2A-GLuc (FIG. 4D). By contrast, as expected, no RSV-$F_{A2}$-specific antibody titers were detected in sera from mice immunized with vectors encoding Firefly luciferase.

Altogether, the data show that the BB21 vector induced potent cellular and humoral immune responses against the encoded antigen, similar in magnitude to those induced by the benchmark vector based on HAdV-26. These immune responses clearly indicate potent immunogenicity of the BB21 vector in mice.

Example 7: Cellular and Humoral Immune Responses Induced by BB24.RSVF-2A-GLuc

The immunogenicity of novel adenoviral vector BB24 was further evaluated using RSV-$F_{A2}$-2A-GLuc (RSVF-2A-GLuc) as a vector-encoded (model) vaccine antigen. Balb/C mice were immunized intramuscularly with Ad26.RSVF-2A-GLuc (positive control), BB24.RSVF-2A-GLuc, or Ad48.RSVF-2A-GLuc (each at $10^8$, $10^9$ and $10^{10}$ viral particles per mouse) or with Ad26.FLuc, BB24.Fluc, or Ad48.FLuc (each at $10^{10}$ viral particles per mouse). According to the same experimental setup as used for BB21.RSVF-2A-GLuc (FIG. 4A), mice were sacrificed at eight weeks post-immunization and blood and splenocytes were collected. Different immune parameters were assessed as described below.

Figure 5A:
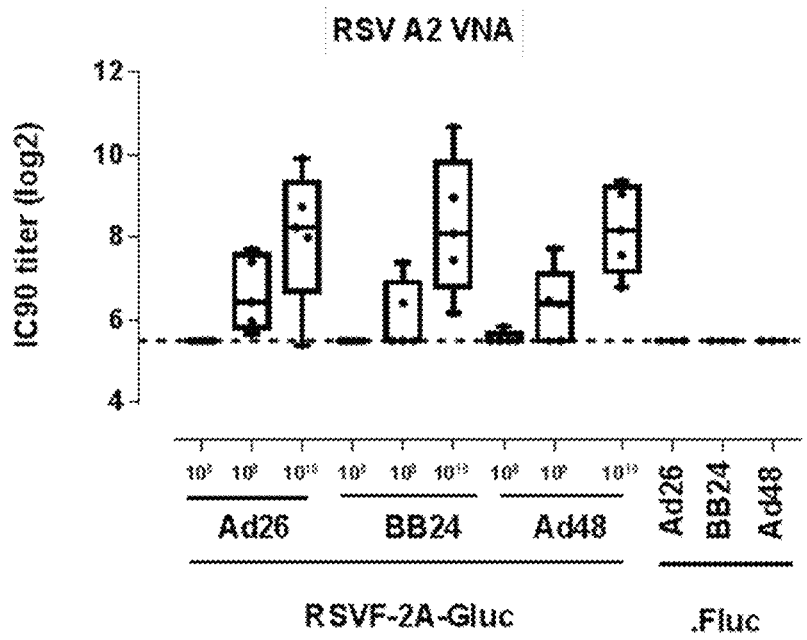
FIG. 5A-FIG. 5C show cellular and humoral responses induced by BB24.RSVF-2A-GLuc.
Figure 5B:
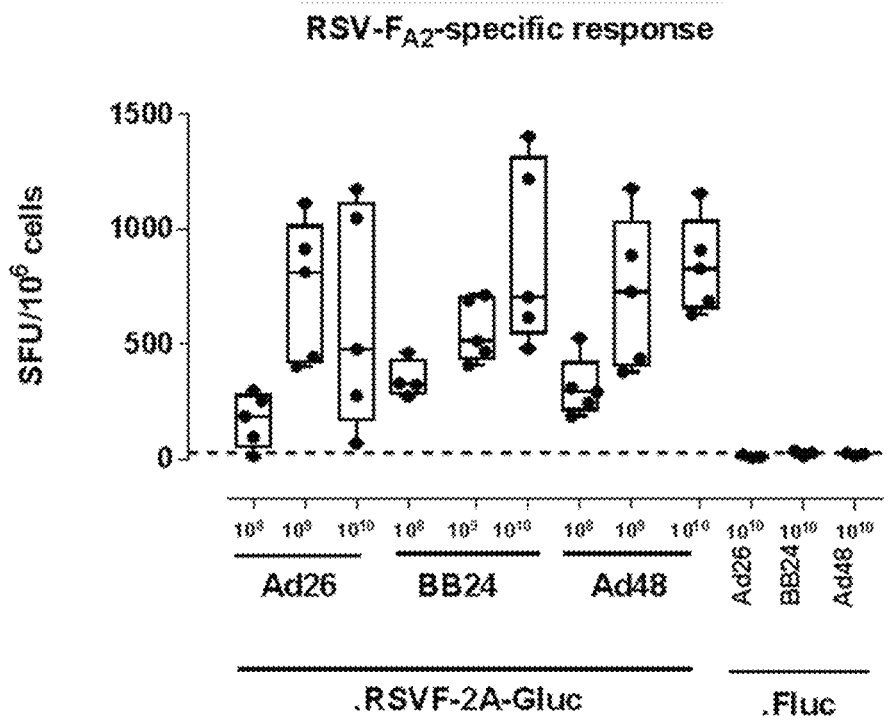

A virus neutralization assay was performed in order to assess the capacity of BB24.RSVF-2A-Gluc to elicit respiratory syncytial virus-neutralizing antibodies. FIG. 5A depicts the respiratory syncytial virus strain A2 (RSV A2) VNA titers measured for sera samples collected eight weeks after immunization. Each dot represents one mouse, the bars represent the group mean, and the dotted line corresponds to the lower limit of quantification (LLOQ=6.88; mean endpoint titer of linearity samples). The results seen for the three vectors are similar: neutralization titers were seen for several or all of the $10^9$ and $10^{10}$ vp-dose immunizations while no, or hardly any, neutralization titers were detected at the $10^8$ vp dose. Induction of cellular immunity against the vector-encoded antigen was evaluated by an RSV-$F_{A2}$-specific ELISPOT assay. To this end, eight weeks after immunization, splenocytes from immunized mice were isolated and stimulated overnight with 15mer overlapping peptides spanning the RSV-$F_{A2}$ protein and cellular immune responses were determined by ex-vivo ELISPOT assay measuring the relative number of IFN-γ-secreting cells. The data show that antigen-specific cellular immune responses elicited by BB24.RSVF-2A-GLuc were dose-dependent and, per dose, at least similar in magnitude to those induced by the comparator vectors, Ad26.RSVF-2A-GLuc and Ad48.RSVF-2A-GLuc (FIG. 5B). As expected, no RSV-$F_{A2}$-specific responses were measured from splenocytes of mice immunized with adenovectors encoding Firefly luciferase.

Figure 5C:
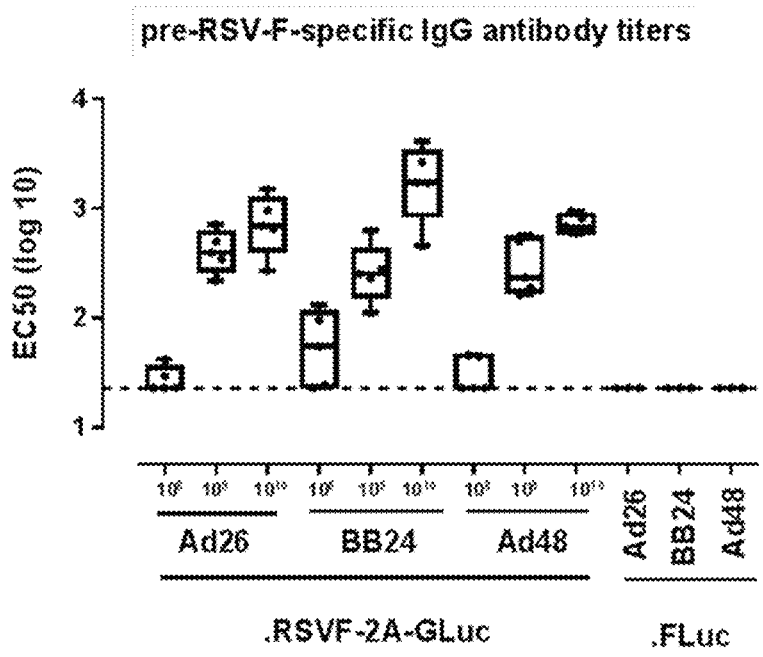

The ability of the RSVF-2A-GLuc-expressing vectors to elicit RSV-$F_{A2}$-specific IgG antibodies was assessed by ELISA. Sera collected 8 weeks post-immunization from the mice immunized with Ad26, Ad48, orBB24 vectors expressing RSVF-2A-GLuc or Firefly luciferase were tested in an anti-RSV $F_{A2}$ IgG antibody ELISA. Specifically, this ELISA detects IgG antibodies capable of binding to a recombinant stable pre-fusion RSV-$F_{A2}$ protein (pre-RSV-F). The results show that BB24.RSVF-2A-GLuc dose-dependently elicited pre-RSV-F-specific IgG antibody titers similar to those induced by Ad26.RSVF-2A-GLuc and Ad48.RSVF-2A-GLuc (FIG. 5C). By contrast, as expected, no RSV-$F_{A2}$-specific titers were detected in sera from mice immunized with the vectors encoding Firefly luciferase.

Altogether, the data show that the BB24 vector induced potent cellular and humoral immune responses against the encoded antigen, similar in magnitude to those induced by the benchmark vector based on HAdV-26. These immune responses clearly indicate potent immunogenicity of the BB24 vector in mice.

Example 8: Cellular and Humoral Immune Responses Induced by Ad4Ptr01-BB24.RSVF-2A-GLuc and Ad4Ptr13-BB21.RSVF-2A-GLuc The respective immunogenicities of novel engineered adenoviral vectors Ad4Ptr01-BB24 and Ad4Ptr13-BB21 were further evaluated using RSV-$F_{A2}$-2A-GLuc (RSVF-2A-GLuc) as a vector-encoded (model) vaccine antigen. Balb/C mice were immunized intramuscularly with Ad26.RSVF-2A-GLuc (positive control), Ad4Ptr01-BB24.RSVF-2A-GLuc, or Ad4Ptr13-BB21.RSVF-2A-GLuc (each at $10^8$, $10^9$ and $10^{10}$ viral particles per mouse) or with Ad26.FLuc, Ad4Ptr01-BB24.FLuc, or Ad4Ptr13-BB21.FLuc (each at $10^{10}$ viral particles per mouse). According to the same experimental setup as used for BB21.RSVF-2A-GLuc (FIG. 4A), blood samples and splenocytes were collected eight weeks post immunization. Different immune parameters were assessed as described below.

Figure 6A:
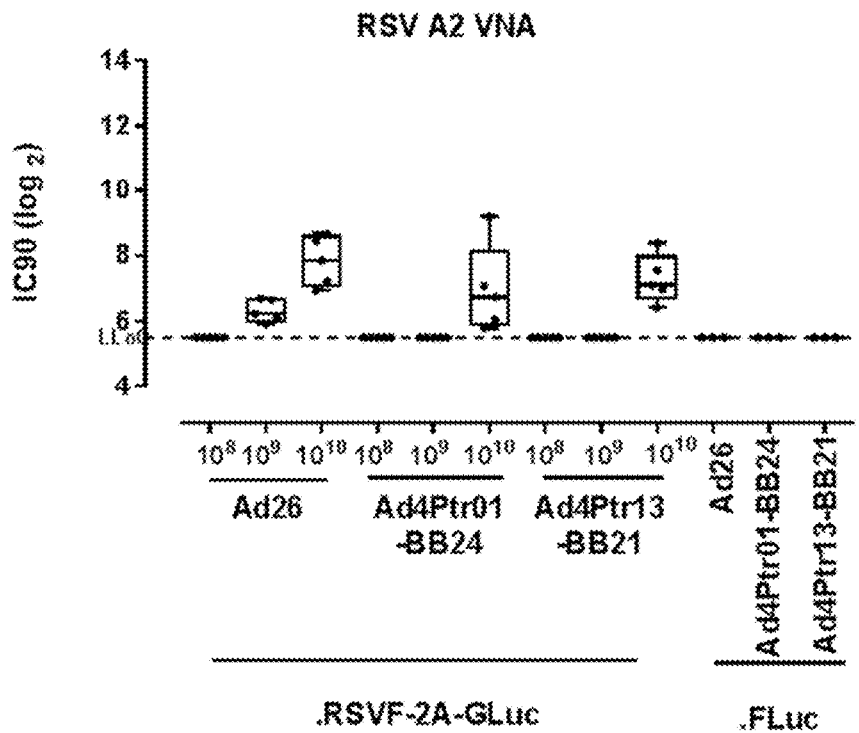
FIG. 6A-FIG. 6C show cellular and humoral responses induced by Ad4Ptr01-BB24.RSVF-2A-GLuc and Ad4Ptr13-BB21.RSVF-2A-GLuc.

Virus neutralization assays were performed in order to assess the capacity of Ad4Ptr01-BB24.RSVF-2A-GLuc and Ad4Ptr13-BB21.RSVF-2A-GLuc to elicit respiratory syncytial virus-neutralizing antibodies. FIG. 6A depicts the respiratory syncytial virus strain A2 (RSV A2) VNA titers measured for sera samples collected eight weeks after immunization. Each dot represents one mouse, the bars represent the group mean, and the dotted line corresponds to the lower limit of quantification (LLOQ=6.88; mean endpoint titer of linearity samples). The results show that the $10^{10}$ vp-dose immunizations with Ad4Ptr01-BB24.RSVF-2A-GLuc and Ad4Ptr13-BB21.RSVF-2A-GLuc both gave rise to RSV A2 neutralization titers.

Figure 6B:
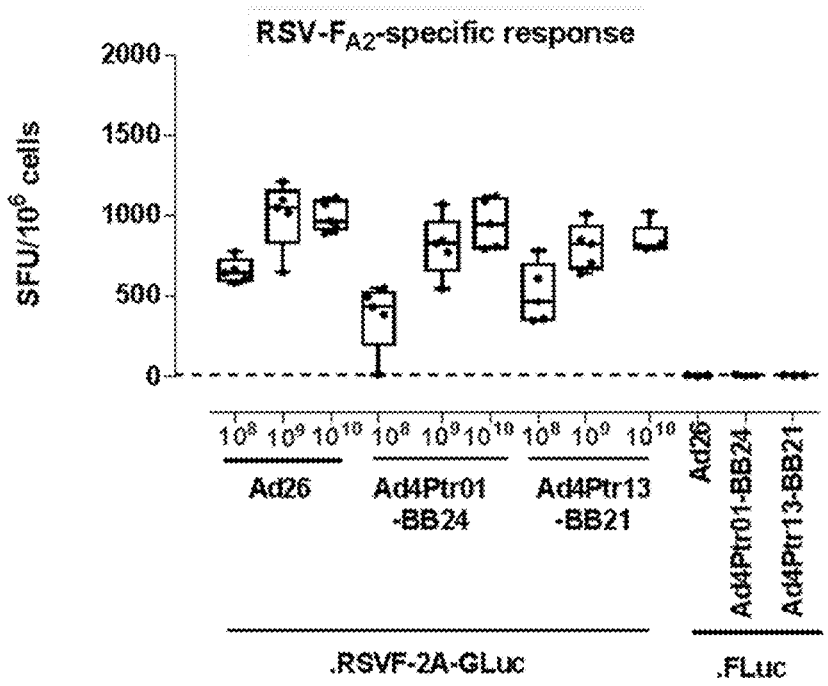

Induction of cellular immunity against the vector-encoded antigen was evaluated by an RSV-$F_{A2}$-specific ELISPOT assay. To this end, eight weeks after immunization, splenocytes from immunized mice were isolated and stimulated overnight with 15mer overlapping peptides spanning the RSV-$F_{24}$ protein and cellular immune responses were determined by ex-vivo ELISPOT assay measuring the relative number of IFN-γ-secreting cells. The data show that both Ad4Ptr13-BB21.RSVF-2A-Gluc and Ad4Ptr01-BB24.RSVF-2A-GLuc were able to elicit dose-dependent antigen-specific cellular immune responses (FIG. 6B). As expected, no RSV-F$_{A2}$-specific responses were measured from splenocytes of mice immunized with adenovectors encoding Firefly luciferase.

Figure 6C:
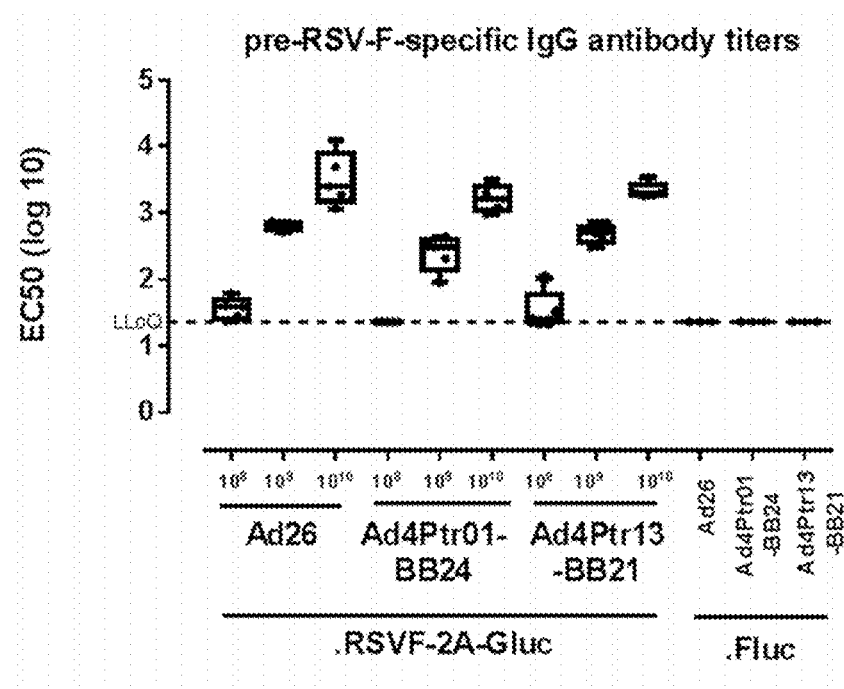

The ability of the RSVF-2A-GLuc-expressing vectors to elicit RSV-F$_{A2}$-specific IgG antibodies was assessed by ELISA. Sera collected 8 weeks post-immunization from the mice immunized with Ad26 (positive control), Ad4Ptr13-BB21, orAd4Ptr01-BB24 vectors expressing RSVF-2A-GLuc or Firefly luciferase were tested in an anti-RSV F$_{A2}$ IgG antibody ELISA. Specifically, this ELISA detects IgG antibodies capable of binding to a recombinant stable pre-fusion RSV-F$_{A2}$ protein (pre-RSV-F). The results show that both Ad4Ptr13-BB21.RSVF-2A-Gluc and Ad4Ptr01-BB24 were able to dose-dependently elicit pre-RSV-F-specific IgG antibody titers (FIG. 6C). As expected, no RSV-F$_{A2}$-specific titers were detected in sera from mice immunized with the vectors encoding Firefly luciferase only.

Altogether, the data show that the RSVF-2A-GLuc-expressing, novel engineered adenoviral vectors Ad4Ptr13-BB21 and Ad4Ptr01-BB24, which respectively comprise a BB21 fiber variant (SEQ ID NO:3) and the BB24 fiber (SEQ ID NO:4), were able to induce significant cellular and humoral immune responses against the encoded antigen. These immune responses clearly indicated good immunogenicity of Ad4Ptr13-BB21 and Ad4Ptr01-BB24 in mice.

Example 9: Evaluation of Serological Cross-Neutralization Among Novel and Existing Adenoviral Vectors For their potential utility as new adenoviral vaccine vectors, the novel adenoviral vectors created herein would preferably be serologically distinct from existing adenoviral vectors currently already in development as vaccine vectors, such as vectors based on human adenovirus serotypes HAdV-5 and HAdV-35. Therefore, cross-neutralization tests were performed among the novel adenoviral vectors BB21, BB24, Ad4Ptr13-BB21, and Ad4Ptr01-BB24 and several existing vectors based on HAdV-4, HAdV-5, HAdV-26, HAdV-35 and HAdV49. To this end, mice antisera, each raised against one of these adenoviral vectors, were tested against each of the different vectors in an adenovirus neutralization assay. The mice antisera used for this assay were collected from Balb/C mice two or eight weeks after their immunization with $10^{10}$ vector particles per mouse. The adenovirus neutralization assay was carried out as described previously (Spangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at a multiplicity of infection of 500 virus particles per cell). Luciferase activity levels in infected cell lysates measured 24 hours post-infection represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 200, 200 to 2,000, and >2,000.

Figure 7:
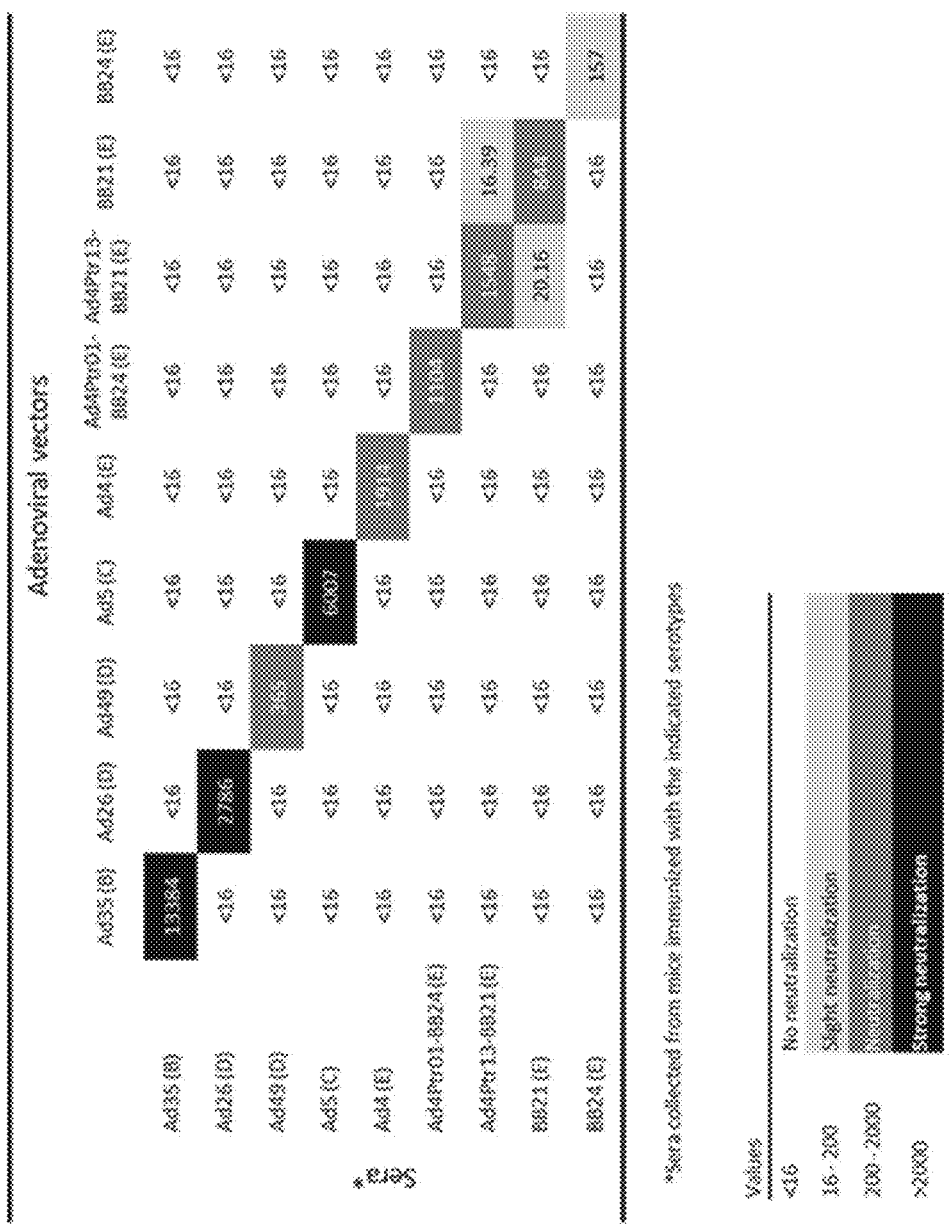
FIG. 7 shows homologous and heterologous adenovirus neutralization titers induced in mice immunized with adenoviral vectors Ad4, Ad5, Ad26, Ad35, Ad49, BB21, BB24, Ad4Ptr13-BB21, and Ad4Ptr01-BB24.

The results show no or very low levels of cross-neutralization among the vectors tested (FIG. 7). The only slight cross-neutralization that was observed was between vectors BB21 and Ad4Ptr13-BB21. The reciprocal cross-neutralization titers seen for these vectors were considerably lower than the respective homologous neutralization titers obtained for these same vectors. Importantly, none of the novel vectors (i.e. BB21, BB24, Ad4Ptr13-BB21, and Ad4Ptr01-BB24) displayed cross-neutralization with the human adenoviral vectors included in the tested panel, i.e. Ad26, Ad35, Ad49, Ad5 and Ad4. Therefore, the new adenoviral vectors BB21, BB24, Ad4Ptr13-BB21, and Ad4Ptr01-BB24 could each potentially be used in combination with one or more of these or other distinct adenoviral vectors in sequential immunizations, for example in the context of a heterologous prime-boost vaccination regimen or, alternatively or additionally, in the context of a series of two or more consecutive vaccination regimens against different diseases or antigens.

Example 10: Seroprevalence of Novel Adenoviral Vectors in Human Populations

Important for their potential use as efficacious vaccine vectors is that the novel adenoviral vectors described herein are not hampered by high levels of pre-existing anti-vector humoral immunity in vaccine target populations. Therefore, vectors BB21, BB24, Ad4Ptr13-BB21, and Ad4Ptr01-BB24 were each evaluated for their seroprevalence within 200 human cohort serum samples from adults, ages 18 to 55 years, living in the United States (US) and the European Union (EU). Each vector was tested for neutralization by the human serum samples by performing a standard adenovirus neutralization assay as carried out in Example 9 and described previously (Sprangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at multiplicity of infection of 500 virus particles per cell). Luciferase activity levels in infected cell lysates, measured 24 hours post-infection, represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 300, 300 to 1000, 1000 to 4000 and >4000.

Figure 8:
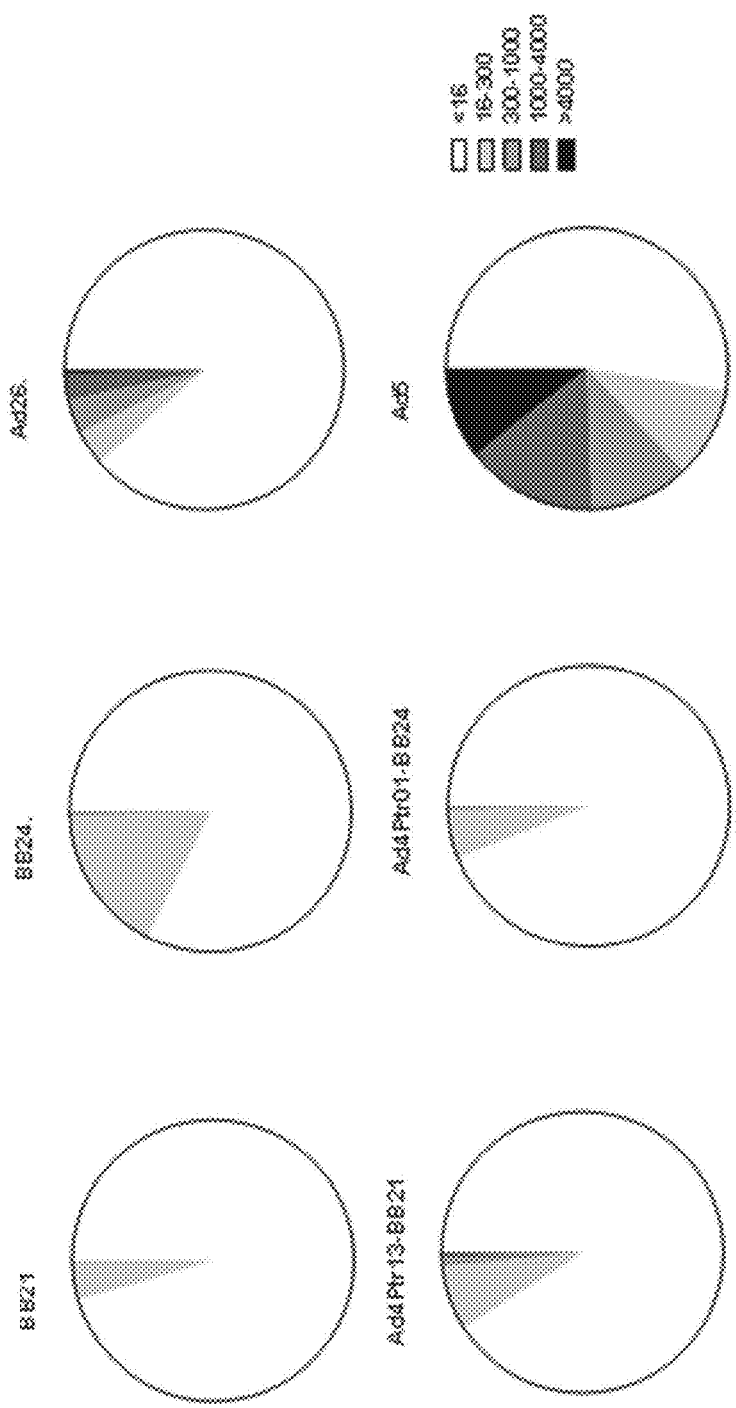
FIG. 8 shows the seroprevalence of Ad5, Ad26, BB21, BB24, Ad4Ptr13-BB21, and Ad4Ptr01-BB24 in 200 human cohort serum samples from adults, age 18 to 55 years, living in the United States (US) and European Union (EU). Neutralization titers measured in these sera against each vector were divided into four categories (<16 (negative), 16 to 300, 300 to 1,000, 1000 to 4000 and >4000), represented in the charts as indicated.

The results indicate that all four novel adenovirus vectors (i.e. BB21, BB24, Ad4Ptr13-BB21, Ad4Ptr01-BB24) have a considerably lower seroprevalence in the human subjects studied than the control Ad5 vector (FIG. 8). Furthermore, vectors BB21, Ad4Ptr13-BB21, and Ad4Ptr01-BB24 additionally displayed a lower seroprevalence than the benchmark Ad26 vector. Moreover, the positive neutralization titers that were seen against the novel vectors were generally quite low, mostly not higher than 300. By contrast, most of the positive neutralization titers found against Ad26 and Ad5 were higher than 300.

Altogether, the above data indicate that pre-existing humoral anti-vector immunity against vectors BB21, BB24, Ad4Ptr13-BB21, and Ad4Ptr01-BB24 can be considered to be low in the evaluated vaccine target populations, suggesting that these vectors have potential as efficacious vaccine vectors in these populations.

Example 11: Adenoviral Vector Productivity in Suspension PER.C6 Cells

Adenovirus vectors to be used in clinical trials and beyond need to be readily producible to high titers in a scalable, serum-free adenovirus production platform. Suspension-adapted PER.C6® cells, also referred to herein as suspension PER.C6 cells or sPER.C6, represent such a platform as they have been shown to support large-scale manufacturing of adenoviral vectors in bioreactors, achieving large quantities of high-titer, clinical grade vector preparations, e.g. of E1-deleted vectors based on HAdV-26 or HAdV-35 (EP 2536829 B1, EP 2350268 B1).

As an initial assessment as to whether the novel vectors described herein would fit sPER.C6 cell-based production processes, small-scale vector productivity experiments were performed on sPER.C6 cells cultured in shaker flasks. These productivity experiments were carried out using the Fluc-encoding versions of the novel vectors described in Examples 1 and 2. Taken along as a benchmark control was the HAdV-26-based vector Ad26.Fluc. Suspension PER.C6 cell cultures, seeded into shaker flasks at a density of $1\times10^6$ cells/ml in a total volume of 10 ml of PERMEXCIS® medium (available from Lonza) supplemented with 4 mM L-Glutamine (Lonza), were infected with the different vectors at different virus particle (VP)-to-cell ratios and then incubated for 4 days. The different VP-to-cell ratios used for infection were 70, 150 and 900. Samples of the infected cell cultures were taken every day and VP titers were determined in these samples by a quantitative PCR (qPCR)-based protocol that employs primers and probe that are specific for the CMV promoter (which is present in all the vectors tested). This protocol entails a DNAse treatment of the test samples prior to the qPCR to remove any free vector DNA (i.e. vector genomes that are not packaged into viral particles).

Figure 17:
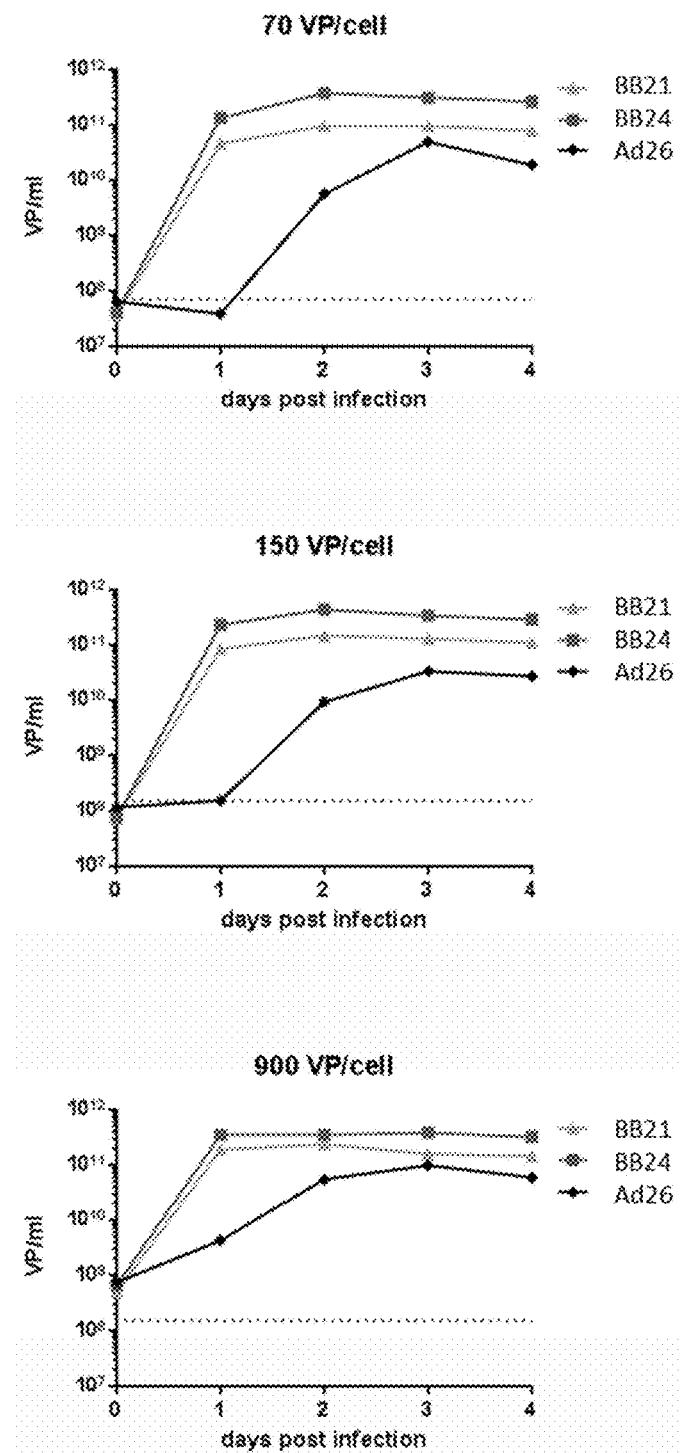
FIG. 17 shows productivity of novel vectors BB21.Fluc and BB24.Fluc in production cell line sPER.C6.
Figure 18:
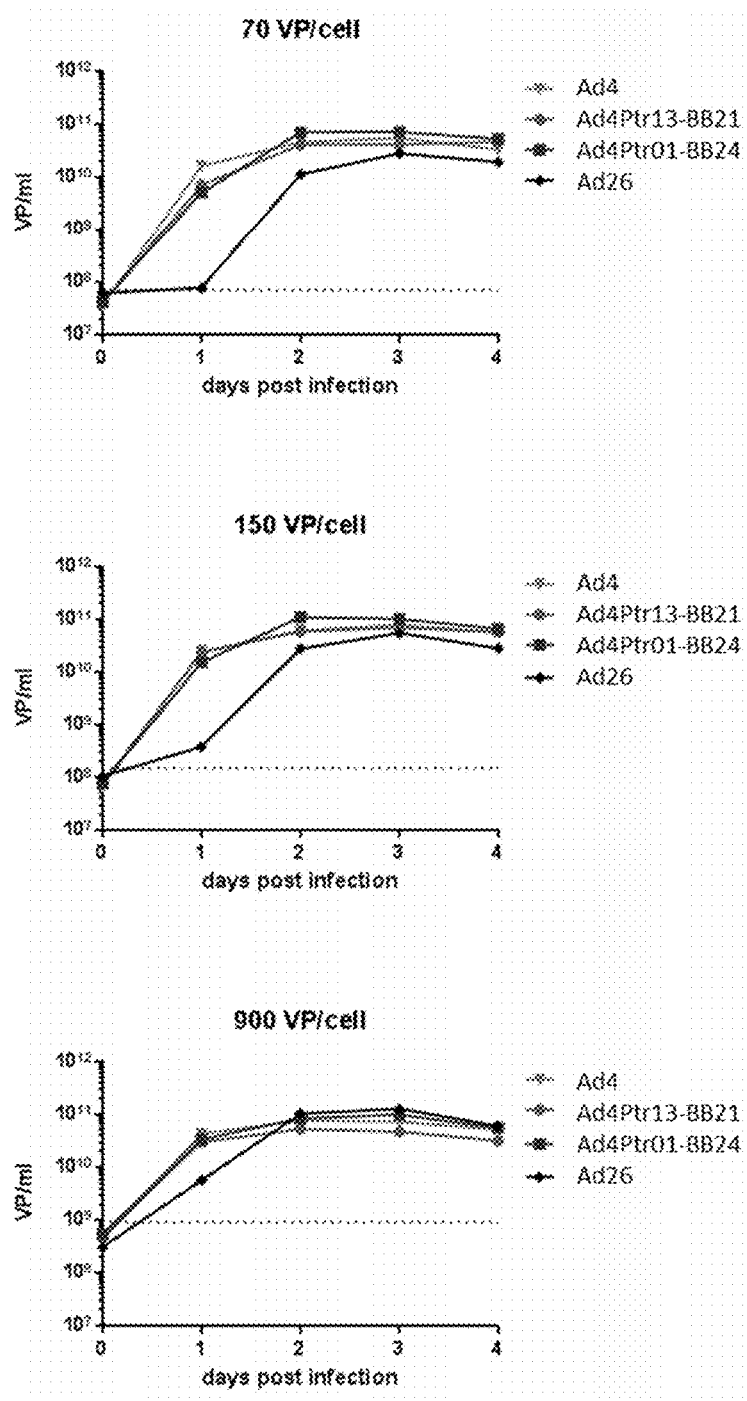
FIG. 18 shows productivity of novel capsid-chimeric vectors Ad4Ptr13-BB21 and Ad4Ptr01-BB24 in production cell line sPER.C6.

The productivity results obtained for novel vectors BB21.FLuc and BB24.Fluc are shown in FIG. 17 while those seen for the new chimeric vectors Ad4Ptr01-BB24.FLuc and Ad4Ptr13-BB21.FLuc, as well as their parental vector Ad4.Fluc, are presented in FIG. 18. BB21.FLuc and BB24.Fluc displayed higher VP titers than the benchmark control vector Ad26.Fluc at all VP-to-cell infection ratios and harvest time points tested. Likewise, the two chimeric vectors Ad4Ptr01-BB24.FLuc and Ad4Ptr13-BB21.FLuc displayed good productivities, yielding VP titers that were either higher than or appearing equivalent to those obtained for Ad26.Fluc (depending on the VP-to-cell infection ratio used). Additionally, these two chimeric vectors showed uncompromised productivities compared to the parental, non-capsid-modified vector Ad4.Fluc.

The above results demonstrate good productivity of each of the novel vectors on a sPER.C6-based, serum-free suspension cell culture model.

Collectively, the studies of humoral and cellular immune responses induced by the novel recombinant adenoviral vectors of the invention, as presented above, clearly indicate potent immunogenicity of these vectors in mice. In addition, the vectors demonstrated to induce no cross-neutralizing antibody responses against certain existing adenoviral vaccine vector candidates (e.g. Ad26 and Ad35) or vice versa, as well as no, or very low, cross-neutralizing antibody responses against each other. Furthermore, the new vectors showed low seroprevalence in humans. Finally, the new vectors can be readily produced at high yields. The combination of low seroprevalence, potent immunogenicity and producibility suggests that the novel adenoviral vectors of the invention can be useful as novel vaccine vector candidates against a variety of pathogens and may additionally have utility in gene therapy and/or diagnostics.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCE LISTING

The patent contains a lengthy sequence listing. A copy of the sequence listing is available in electronic form from the USPTO web site (https://seqdata.uspto.gov/?pageRequest=docDetail&DocID=US11872281B2). An electronic copy of the sequence listing will also be available from the USPTO upon request and payment of the fee set forth in 37 CFR 1.19(b)(3).

It is claimed:

1. An adenoviral vector comprising:
   (a) at least one transgene; and
   (b) a nucleic acid sequence encoding a fiber polypeptide, wherein the fiber polypeptide comprises an amino acid sequence with at least 98% identity to amino acids 6-375 of SEQ ID NO:2.

2. The adenoviral vector of claim 1, wherein the fiber polypeptide comprises an amino acid sequence selected from a BB21 fiber polypeptide (SEQ ID NO:2), a BB21 fiber variant polypeptide (SEQ ID NO:3), or a BB24 fiber polypeptide (SEQ ID NO:4).

3. The adenoviral vector of claim 1, further comprising a nucleic acid sequence encoding a hexon polypeptide comprising a hexon hypervariable regions-encompassing polypeptide comprising an amino acid sequence selected from SEQ ID NO:5 or SEQ ID NO:6.

4. The adenoviral vector of claim 3, wherein the hexon polypeptide comprises an amino acid sequence selected from a BB21 hexon polypeptide (SEQ ID NO:7) or a BB24 hexon polypeptide (SEQ ID NO:8).

5. The adenoviral vector of claim 1, wherein the adenoviral vector further comprises an E1 deletion.

6. The adenoviral vector of claim 1, wherein the adenoviral vector further comprises an E3 deletion.

7. The adenoviral vector of claim 1, wherein the adenoviral vector is a chimeric adenoviral vector comprising one or more human adenoviral nucleic acid sequences.

8. The adenoviral vector of claim 7, wherein the human adenoviral nucleic acid sequences are from human adenovirus-4, human adenovirus-5, human adenovirus-26, or human adenovirus-35.

9. The adenoviral vector of claim 8, wherein the adenoviral vector comprises a human adenovirus-5 (hAdV-5) E4 orf6.

10. The adenoviral vector of claim 1, wherein the transgene is located at an E1 deletion site, at an E3 deletion site, or adjacent to a right inverted terminal repeat (rITR).

11. The adenoviral vector of claim 1, wherein the adenoviral vector comprises a nucleic acid sequence selected from the group consisting of SEQ ID NO:28, SEQ ID NO:29, SEQ ID NO:30, and SEQ ID NO:31.

12. The adenoviral vector of claim 1, wherein the adenoviral vector comprises a nucleic acid sequence selected from SEQ ID NO:53 or SEQ ID NO:57.

13. A vaccine comprising an adenoviral vector according to claim 1 and a pharmaceutically acceptable carrier.

14. A method for inducing an immune response in a subject in need thereof, the method comprising administering to the subject the vaccine of claim 13.

15. A method of producing a vaccine, comprising combining an adenoviral vector according to claim 1 with a pharmaceutically acceptable carrier.

16. An isolated recombinant cell comprising the adenoviral vector of claim 1.

17. An isolated recombinant cell comprising the adenoviral vector of claim 2.

18. An immunogenic composition comprising the adenoviral vector of claim 1.

19. A vaccine comprising an adenoviral vector according to claim 2, wherein the transgene encodes an antigen, and a pharmaceutically acceptable carrier.

20. A vaccine comprising an adenoviral vector according to claim 3, wherein the transgene encodes an antigen, and a pharmaceutically acceptable carrier.

21. A vaccine comprising an adenoviral vector according to claim 4, wherein the transgene encodes an antigen, and a pharmaceutically acceptable carrier.

22. A vaccine comprising an adenoviral vector according to claim 5, wherein the transgene encodes an antigen, and a pharmaceutically acceptable carrier.

23. A vaccine comprising an adenoviral vector according to claim 8, wherein the transgene encodes an antigen, and a pharmaceutically acceptable carrier.

24. A method of producing a vector, comprising;
(a) growing the recombinant cell of claim 16 under conditions for production of the vector;
(b) isolating the vector from the recombinant cell.

25. A method of inducing an immune response in a subject in need thereof, comprising administering to the subject the immunogenic composition of claim 1.

* * * * *